United States Patent
Glombik et al.

(10) Patent No.: US 7,956,077 B2
(45) Date of Patent: *Jun. 7, 2011

(54) 2-{-3,'2-(PHENYL)-OXAZOL-4-YLMETHOXYL-CYCLOHEXYL METHOXY}-PROPIONIC ACID DERIVATIVES USED AS PEROXISOME PROLIFERATOR-ACTIVATED RECEPTOR (PPAR) LIGANDS FOR THE TREATMENT OF HYPERLIPIDEMIA AND DIABETES

(75) Inventors: Heiner Glombik, Hofheim (DE); Christian Stapper, Mainz (DE); Eugen Falk, Frankfurt (DE); Stefanie Keil, Hofheim (DE); Hans-Ludwig Schaefer, Hochheim (DE); Wolfgang Wendler, Selters (DE); Stephanie Knieps, Sulzbach (DE)

(73) Assignee: Sanofi-Aventis Deutschland GmbH, Frankfurt Am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/671,673

(22) Filed: Feb. 6, 2007

(65) Prior Publication Data

US 2007/0197613 A1    Aug. 23, 2007

Related U.S. Application Data

(63) Continuation of application No. PCT/EP2005/008281, filed on Jul. 30, 2005.

(30) Foreign Application Priority Data

Aug. 14, 2004   (DE) .......................... 10 2004 039 532

(51) Int. Cl.
*A01N 43/76* (2006.01)
*C07D 263/34* (2006.01)
(52) U.S. Cl. ........................ 514/374; 548/235
(58) Field of Classification Search ............... None
See application file for complete search history.

(56) References Cited

U.S. PATENT DOCUMENTS

| | | | |
|---|---|---|---|
| 7,259,177 B2 * | 8/2007 | Stapper et al. | 514/374 |
| 7,335,671 B2 * | 2/2008 | Stapper et al. | 514/340 |
| 2008/0015238 A1 * | 1/2008 | Stapper et al. | 514/374 |

FOREIGN PATENT DOCUMENTS

| | | |
|---|---|---|
| WO | WO 03/020269 | 3/2003 |
| WO | WO 2004/076427 | 9/2004 |

OTHER PUBLICATIONS http://www.fda.gov/cder/present/DIA2006/EI-Hage_Safety.pdf.*
Zips et al, "new anticancer agents: in vitro and in vivo", in vivo, 2005, 19, 1-7.*
Megard et al., "A co-culture based model of human blood-brain, barrier: application to active transport of indinavir and in vivo-in vitro correlation", Brain Research, 927, 2002, 153-167.*
Fact sheet Alzheimers association, 2 pages.*
http://www.mayoclinic.com/health/alzheimers-disease/DS00161/DSECTION=3.*
http://www.medindia.net/patients/patientinfo/Alzheimers_treatment.htm.*
Hacks Chemical Dictionary, Fourth Edition, Julius Grant, 1972, p. 203.*
Newman et al., DDT vol. 8, Oct. 2003, p. 898-90.*
Chawla et al., CRIPS vol. 5, No. 1, Jan.-Mar. 2004, p. 9-12.*
U.S. Appl. No. 12/013,8, dated Feb. 2004, Stapper et al.*

* cited by examiner

*Primary Examiner* — Sun Jae Y. Loewe
(74) *Attorney, Agent, or Firm* — Scully, Scott, Murphy & Presser, P.C.

(57) ABSTRACT

The present invention comprises compounds and compositions for the treatment of metabolic disorders and more particularly, those insulin-related metabolic disorders of the blood such as hyperlipidemia, diabetes, insulin-resistance and the like comprising acetic acid derivatives with cyclohexylmethoxy substituents and their salts. Known as peroxisome proliferator-activated receptors (PPAR) agonists/antagonists, the invention relates to compounds of formula I

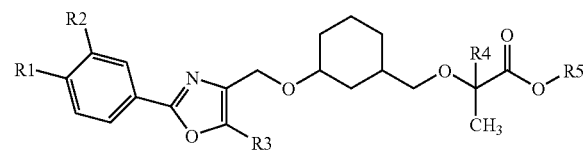

wherein the various substituent R-groups are more specifically defined herein.

15 Claims, No Drawings

2-{-3,'2-(PHENYL)-OXAZOL-4-YLMETHOXYL-CYCLOHEXYL METHOXY}-PROPIONIC ACID DERIVATIVES USED AS PEROXISOME PROLIFERATOR-ACTIVATED RECEPTOR (PPAR) LIGANDS FOR THE TREATMENT OF HYPERLIPIDEMIA AND DIABETES

CROSS-REFERENCE TO RELATED APPLICATIONS

This application is a continuation of International Patent Application No. PCT/EP2005/008281 filed on Jul. 30, 2005 which is incorporated herein by reference in its entirety which also claims the benefit of priority of German Patent Application No. 10/2004 039532.2 filed on Aug. 14, 2004.

FIELD OF THE INVENTION

The invention relates generally to compounds and compositions for the treatment of metabolic disorders and more particularly, those insulin-related metabolic disorders of the blood such as hyperlipidemia and diabetes and the like. More specifically, the present invention relates to compounds that therapeutically modulation and control lipid and/or carbohydrate metabolism and are thus suitable for the prevention and/or treatment of diseases such as type-2 diabetes and atherosclerosis, and the diverse manifestations thereof. Even more specifically, the present invention relates to acetic acid derivatives with cyclohexylmethoxy substituents, their salts and functional derivatives thereof as well as methods for their preparation and formulation as pharmaceutical compositions for the treatment of said disorders.

BACKGROUND OF THE INVENTION

Compounds comprising structures similar to the acetic acid derivatives with cyclohexylmethoxy substituents and their salts as described herein are known and have also been described in the art for the treatment of hyperlipidemia and diabetes (see WO 2004/076427 to Stapper et. al.).

The compounds of the present invention are highly effective in the therapeutic modulation of lipid and/or carbohydrate metabolism and are therefore useful in the prevention and/or treatment of diseases such as type-2 diabetes and atherosclerosis, and the many other diverse cardiovascular, among others, manifestations therefrom. These compounds have been found to exhibit peroxisome proliferator-activated receptor (PPAR) agonist/antagonist activity, in particular, an excellent PPARalpha modulatory effect as well as a correspondingly excellent PPARgamma modulatory effect.

The peroxisome proliferator-activated receptors (PPAR) are transducer proteins belonging to the steroid/thyroid/retinoid receptor superfamily. The PPAR receptors were originally identified as orphan receptors without known ligands, but were known for their ability to mediate the pleiotropic effects of fatty acid peroxisome proliferators. These receptors function as ligand-regulated transcription factors that control the expression of target genes by binding to their responsive DNA sequences as heterodimers with RXR. The target genes encode enzymes involved in a number of metabolic and cell growth/cell proliferation/cell differentiation inductions. These then provide targets for the development of therapeutic agents for the treatment of metabolic and central nervous system disorders, among others.

PPAR agonists are well known and have been described in the prior art, see U.S. Pat. No. 6,200,995 to De La Brouse-Elwood et. al.; WO 03/043997 to Johnston et. al. and WO 01/00603 and WO 02/092590 to Keil et. al.). comprising an oxadiazolone feature as inhibitors of factor Xa were disclosed in DE 101 12 768 A1 and oxodiazolones have also been described as oral hypoglycemic agents in WO 96/13264.

SUMMARY OF THE INVENTION

The present invention comprises compounds and compositions for the treatment of metabolic disorders and more particularly, those insulin-related metabolic disorders of the blood such as hyperlipidemia, diabetes, insulin-resistance and the like comprising acetic acid derivatives with cyclohexylmethoxy substituents and their salts. Known as peroxisome proliferator-activated receptors (PPAR) agonists/antagonists, the invention relates to compounds of formula I

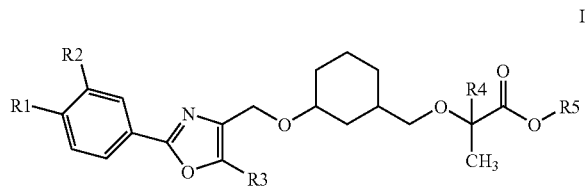

in which the meanings for the respective R-group substituents are defined herein:

DETAILED DESCRIPTION OF THE INVENTION

The present invention comprises compounds and compositions for the treatment of metabolic disorders and more particularly, those insulin-related metabolic disorders of the blood such as hyperlipidemia and diabetes and the like comprising acetic acid derivatives with cyclohexylmethoxy substituents and their salts. Known as peroxisome proliferator-activated receptors (PPAR) agonists/antagonists, the invention relates to compounds of the formula I

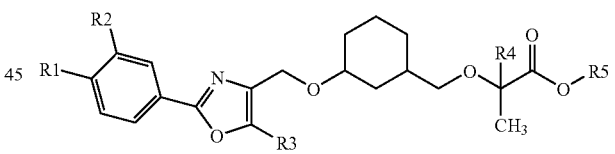

Wherein the R-group substituents are defined as follows:
R1 is selected from the group consisting of H or (C1-C6)-alkyl;
R2 is selected from the group consisting of H, O-(C1-C3)-alkyl, CF$_3$; or
optionally, R1 and R2 are fused together with the phenyl ring to form a naphthyl group;
R3 is selected from the group consisting of (C1-C6)-alkyl;
R4 is selected from the group consisting of (C1-C6)-alkyl or benzyl;
R5 is selected from the group consisting of H or (C1-C6)-alkyl;
and the salts, solvates and functional derivatives thereof.
Preferred compounds of formula I are those in which
R1 is selected from the group consisting of is H, methyl, propyl or butyl;
R2 is selected from the group consisting of is H, methoxy, CF$_3$; or optionally, R1 and R2 are fused together with the phenyl ring to form a naphthyl group R3 is selected from the group consisting of methyl, ethyl or propyl;

R4 is selected from the group consisting of methyl, propyl or benzyl; and

R5 is H.

Particularly preferred compounds of the formula 1 are those in which

R1 or R2 is H;

or R4 is methyl.

The R-group substituents R1, R2, R3, R4 and R5 may be either straight-chain or branched.

The compounds of the formula I comprise at least two centers of asymmetry and may optionally comprise more in addition. The compounds of the formula I may therefore be in the form of their racemates, racemic mixtures, pure enantiomers, diastereomers and iastereomeric mixtures. The present invention includes all the isomeric forms of the compounds of formula I. These isomeric forms can be obtained and isolated by methods well known in the art.

Pharmaceutically acceptable salts of the claimed compounds are particularly suitable or medical applications because their solubility in water is greater than that of the initial or basic. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Even those salts with a pharmaceutically unacceptable anion such as, for example, trifluoroacetate, however, also fall within the scope of the present invention since these may also be useful intermediates for the preparation or purification of pharmaceutically acceptable salts and/or for use in non-therapeutic in vitro applications.

The term "physiologically functional derivative" used herein refers to any physiologically tolerated derivative of a compound of formula I of the invention, for example an ester, which on administration to a mammal such as, for example, a human is able to form (directly or indirectly) a compound of the formula I or an active metabolite thereof.

Physiologically functional derivatives also include pro-drugs of the compounds of the invention, as described, for example, in H. Okada et al., Chem. Pharm. Bull. 1994, 42, 57-61. Such pro-drugs can be metabolized in vivo to a compound of the invention. These pro-drugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

This invention further relates to the use of the compounds of the formula I and their pharmaceutical compositions as peroxisome proliferator-activated receptor (PPAR) receptor ligands. The PPAR receptor ligands of the invention are suitable as modulators of PPAR receptor activity.

As discussed briefly earlier, peroxisome proliferator-activated receptors (PPAR) are transcription factors which can be activated by ligands and belong to the class of nuclear hormone receptors. There are three PPAR isoforms, PPARalpha, PPARgamma and PPARdelta, which are encoded by different genes (see *Peroxisome Proliferator-Activated Receptor (PPAR): Structure, Mechanisms of Activation and Diverse Functions:* Motojima K, Cell Struct Funct., 1993 October, 18(5), 267-77). Which is hereby incorporated by reference.

Two variants of PPARgamma exist, PPARgamma$_1$ and PPARgamma$_2$, which are the result of an alternative use of promoters and differential mRNA splicing (Vidal-Puig et al. J. Clin. Invest., 97:2553-2561, 1996). Different PPAR receptors have different tissue distribution and modulate different physiological functions. The PPAR receptors play a key role in various aspects of the regulation of a large number of genes, the products of which genes are directly or indirectly crucially involved in lipid and carbohydrate metabolism. Thus, for example, PPARalpha receptors play an important part in the regulation of fatty acid catabolism or lipoprotein metabolism in the liver, while PPARgamma is crucially involved in regulating adipose cell differentiation.

In addition, however, PPAR receptors are also involved in the regulation of many other physiological processes, including those which are not directly connected with carbohydrate or lipid metabolism. The activity of different PPAR receptors can be modulated by various fatty acids, fatty acid derivatives and synthetic compounds to varying extents. For relevant reviews about functions, physiological effect and pathophysiology, see: Joel Berger et al., Annu. Rev. Med., 2002, 53, 409-435; Timothy Wilson et al., J. Med. Chem., 2000, Vol. 43, No. 4, 527-550; Steven Kliewer et al., Recent Prog Horm Res., 2001, 56, 239-63.which are hereby incorporated herein by reference.

The present invention further relates to compounds of formula I suitable for modulating the activity of PPAR receptors, especially the activity of PPARalpha and PPARgamma. Depending on the modulation profile, the compounds of the formula I are suitable for the treatment, control and prophylaxis of the indications described hereinafter, and for a number of other pharmaceutical applications connected thereto (see, for example, Joel Berger et al., Annu. Rev. Med., 2002, 53, 409-435; Timothy Wilson et al. J. Med. Chem., 2000, Vol. 43, No. 4, 527-550; Steven Kliewer et al., Recent Prog Horm Res. 2001; 56: 239-63; Jean-Charles Fruchart, Bart Staels and Patrick Duriez: PPARS, *Metabolic Disease and Arteriosclerosis*, Pharmacological Research, Vol. 44, No. 5, 2001; Sander Kersten, Beatrice Desvergne & Walter Wahli: *Roles of PPARs in Health and Disease*, NATURE, VOL 405, 25 MAY 2000; Ines Pineda Torra, Giulia Chinetti, Caroline Duval, Jean-Charles Fruchart and Bart Staels: Peroxisome Proliferator-Activated Receptors: From Transcriptional Control to Clinical Practice, Curr Opin Lipidol 12: 2001, 245-254).

Compounds of this type are particularly suitable for the treatment and/or prevention of 1. —Disorders of fatty acid metabolism and glucose utilization disorders Metabolic disorders in which insulin resistance is involved 2. Diabetes mellitus, especially type-2 diabetes, including the prevention of the disease states or injury manifestations associated therewith. Particular aspects in this connection are hyperglycemia, improvement in insulin resistance, improvement in glucose tolerance,
protection of the pancreatic B cells
prevention of macro- and microvascular disorders
3. Dyslipidemias and the disease states or injury manifestations associated therewith such as atherosclerosis, coronary heart disease, cerebrovascular disorders etc, especially those which are characterized by one or more of the following factors:
high plasma triglyceride concentrations, high postprandial plasma triglyceride concentrations,
low HDL cholesterol concentration
low ApoA lipoprotein concentrations
high LDL cholesterol concentrations
small dense LDL cholesterol particles
high ApoB lipoprotein concentrations
4. Various other conditions which may be associated with the metabolic syndrome, such as:
obesity (excess weight), including central obesity
thromboses, hypercoagulable and prothrombotic stages (arterial and venous)
high blood pressure
heart failure such as that following myocardial infarction, hypertensive heart disease or cardiomyopathy
5. Other disorders or conditions in which inflammatory reactions or cell differentiation are involved:
Atherosclerosis such as coronary sclerosis including angina pectoris or myocardial infarction and stroke
vascular restenosis or reocclusion
chronic inflammatory bowel disease such as Crohn's disease and ulcerative colitis
pancreatitis
other inflammatory states
retinopathy
adipose cell tumors
lipomatous carcinomas such as, for example, liposarcomas
solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc.
acute and chronic myeloproliferative disorders and lymphomas
angiogenesis
neurodegenerative disorders
Alzheimer's disease
multiple sclerosis
Parkinson's disease
erythemato-squamous dermatoses such as, for example, psoriasis
acne vulgaris
other skin disorders and dermatological conditions which are modulated by PPAR ligands
eczemas and neurodermatitis
dermatitis such as, for example, seborrheic dermatitis or photodermatitis
keratitis and keratoses such as, for example, seborrheic keratoses, senile keratoses, actinic keratosis, photo-induced keratoses or keratosis follicularis
keloids and keloid prophylaxis
warts, including condylomata or condylomata acuminata
human papilloma viral (HPV) infections such as, for example, venereal warts, viral warts such as, for example, molluscum contagiosum, leukoplakia
papular dermatoses such as, for example, lichen planus
skin cancer such as, for example, basal-cell carcinomas, melanomas or cutaneous T-cell lymphomas
localized benign epidermal tumors such as, for example, keratoderma, epidermal naevi
chilblains
high blood pressure
syndrome X
polycystic ovary syndrome (PCOS)
asthma
osteoarthritis
lupus erythematosus (LE) or inflammatory rheumatic disorders such as, for example, rheumatoid arthritis
vasculitis
wasting (cachexia)
gout
ischemia/reperfusion syndrome
acute respiratory distress syndrome (ARDS)

The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically of 0.01 mg and 50 mg) per day and per kilogram of bodyweight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, capsules or tablets, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful to the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (i. e., sublingual) and parenteral (i.e., subcutaneous, intramuscular, intradermal or intravenous) administration, although the most suitable mode of administration depends in each individual case, the nature and severity of the condition to be treated and chemical characteristics of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropyl methylcellulose phthalate and anionic polymers of methacrylic acid and methyl methacrylate.

Suitable pharmaceutical preparations for oral administration may be in the form of separate units such as, for example, capsules, cachets, slow-dissolving oral tablets or lozenges, each of which contain a defined amount of the compound of formula l; as powders or granules, as a solution or suspension in an aqueous or non-aqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agents in a suitable machine. Molded tablets can be produced by molding the compound, which is in powder form and is moistened with an inert liquid diluent, in a suitable machine.

Pharmaceutical compositions which are suitable for per-oral (sublingual) administration comprise slow-dissolving oral tablets or lozenges, which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986) which is also incorporated herein by reference.

The compounds of the formula I are distinguished by favorable effects on metabolic disorders. They beneficially influence lipid and sugar metabolism, in particular they lower the triglyceride level and are suitable for the prevention and treatment of type II diabetes and arteriosclerosis and the diverse disease states or injury manifestations associated therewith.

The compounds of the present invention can be administered alone or in combination with one or more secondary pharmacologically active substances which also are therapeutically effective when administered to individuals with metabolic disturbances or disorders frequently associated therewith. Examples of such pharmaceutical actives include, but are not limited to:

1. active compounds which lower blood glucose levels, i.e., anti-diabetic agents,
2. active compounds for the treatment of dyslipidemias,
3. anti-atherosclerotic compounds
4. anti-obesity agents,
5. anti-inflammatory compounds
6. anti-cancer compounds
7. anti-thrombotic active compounds
8. active compounds for the treatment of high blood pressure
9. active compounds for the treatment of heart failure, and,
10. active compounds for the treatment and/or prevention of complications caused by diabetes or associated with diabetes.

When combined with the compounds of the invention of formula I, there will likely result in a synergistic therapeutic effect. Administration of the active ingredient combination can take place either by separate administration of the active ingredients to the patient or in the form of combination products in which a plurality of active ingredients are present in one pharmaceutical preparation. Specific examples of these secondary actives include:

Anti-diabetic Agents

Suitable anti-diabetic agents are disclosed for example in the Rote Liste 2001, chapter 12 or in the USP Dictionary of USAN and International Drug Names, US Pharmacopeia, Rockville 2003. Anti-diabetic agents include insulin and insulin derivatives such as, for example, Lantus® (see www-.lantus.com) or Apidra®, and other fast-acting insulins (see U.S. Pat. No. 6,221,633 to Ertle et.al.), GLP-1 receptor modulators as described in WO 01/04146 or else, for example, those disclosed in U.S. Pat. No. 6,268,343 to Knudsen et. al. (Novo Nordisk A/S).

The orally effective hypoglycemic active ingredients include, preferably, sulfonylureas, biguanidines, meglitinides, oxadiazolidinediones, thiazolidinediones, glucosidase inhibitors, glucagon antagonists, oral GLP-1 agonists, DPP-IV inhibitors, potassium channel openers such as, for example, those disclosed in U.S. Pat. Nos. 6,225,310 and 5,889,002 both to Nielsen et. al., insulin sensitizers, inhibitors of liver enzymes involved in the stimulation of gluconeogenesis and/or glycogenolysis, modulators of glucose uptake, compounds which alter lipid metabolism and lead to a change in the blood lipid composition, compounds which reduce food intake or food absorption, PPAR and PXR modulators and active ingredients which act on the ATP-dependent potassium channel of beta cells.

In one embodiment of the invention, the compounds of formula I are administered in combination with insulin.

In a second embodiment of the invention, the compounds of formula I are formulated in combination with substances which influence hepatic glucose production such as, for example, glycogen phosphorylase inhibitors (see: WO 01/94300, WO 02/096864, WO 03/084923, WO 03/084922, WO 03/104188).

In a third embodiment, the compounds of the formula I are administered in combination with a sulfonylurea such as, for example, tolbutamide, glibenclamide, glipizide or glimepiride.

In another embodiment, the compounds of the formula I are formulated in combination with an active ingredient which acts on the ATP-dependent potassium channel of the beta cells, such as, for example, tolbutamide, glibenclamide, glipizide, glimepiride or repaglinide.

In yet another embodiment of the present invention, the compounds of the formula I are administered in combination with a biguanide such as, for example, mefformin.

In a further embodiment, the compounds of the formula I are administered in combination with a meglitinide such as, for example, repaglinide.

The compounds of formula I may also be administered in combination with a thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In another embodiment of the invention, the compounds of the formula I are in combined with a dipeptidyl peptidase IV (DPP-IV) inhibitor as described in WO98/19998, WO99/61431, WO99/67278, WO99/67279, WO01/72290, WO 02/38541, WO03/040174, in particular P 93/01 (1-cyclopentyl-3-methyl-1-oxo-2-pentanammonium chloride), P-31/98, LAF237 (1-[2-[3-hydroxyadamant-1-ylamino)acetyl]pyrrolidine-2-(S)-carbonitrile), TS021 ((2S, 4S)-4-fluoro-1-[[(2-hydroxy-1,1-dimethylethyl)amino]acetyl]pyrrolidine-2-carbonitrile monobenzenesulfonate).

In yet another embodiment of the invention, the compounds of the formula I are administered in combination with a PPARgamma agonist such as, rosiglitazone and/or, pioglitazone.

The compounds of the formula I may also be administered in combination with compounds with an inhibitory effect on SGLT-1 and/or 2, as disclosed directly or indirectly for example in WO 2004/007517, WO 2004/052902 and WO 2004/052903.

In one embodiment, the compounds of formula I are administered in combination with an α-glucosidase inhibitor such as, for example, miglitol or acarbose.

In one embodiment, the compounds of formula I are administered in combination with more than one of the aforementioned compounds, e.g. in combination with a sulfonylurea and mefformin, a sulfonylurea and acarbose, repaglinide and metformin, insulin and a sulfonylurea, insulin and metformin, insulin and troglitazone, insulin and lovastatin, etc.

In one embodiment of the invention, the compounds of the formula I are administered in combination with an HMGCoA reductase inhibitor such as lovastatin, fluvastatin, pravastatin, simvastatin, ivastatin, itavastatin, atorvastatin and/or, rosuvastatin.

In one embodiment of the invention, the compounds of the formula I are administered in combination with a bile acid absorption inhibitor (see, for example, U.S. Pat. Nos. 6,245, 744; 6,221,897 and 6,277,831 all to Frick et. al, EP 0683 773, and EP 0683 774).

In one embodiment of the invention, the compounds of the formula I are administered in combination with a polymeric bile acid adsorbent such as, for example, cholestyramine or colesevelam.

In one embodiment of the invention, the compounds of the formula I are administered in combination with a cholesterol absorption inhibitor as described for example in WO 0250027, or ezetimibe, tiqueside, pamaqueside.

In another embodiment of the invention, the compounds of formula I are administered in combination with an LDL receptor inducer (see, for example, U.S. Pat. No. 6,342,512 to Kirsch et. al.).

In one embodiment, the compounds of formula I are administered in combination with bulking agents, preferably insoluble bulking agents (see, for example, carob/Caromax® (Zunft H J; et al., *Carob pulp Preparation for Treatment of Hypercholesterolemia*, ADVANCES IN THERAPY (2001 September-October), 18(5), 230-6). Caromax® is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compounds of formula I are administered in combination with a PPARalpha agonist.

In another embodiment of the invention, the compounds of the formula I are administered in combination with a mixed PPAR alpha/gamma agonist such as, for example, AZ 242 (Tesaglitazar, (S)-3-(4-[2-(4-methane-sulfonyloxyphenyl) ethoxy]phenyl)-2-ethoxypropionic acid), BMS 298585 (N-[(4-methoxyphenoxy)carbonyl]-N-[[4-[2-(5-methyl-2-phenyl-4-oxazolyl)-ethoxy]phenyl]methyl]glycine) or as described in WO 99/62872, WO 99/62871, WO 01/40171, WO 01/40169, WO96/38428, WO 01/81327, WO 01/21602, WO 03/020269, WO 00/64888 or WO 00/64876.

In a further embodiment of the invention, the compounds of the formula I are administered in combination with a fibrate such as, for example, fenofibrate, gemfibrozil, clofibrate, bezafibrate.

In one embodiment of the invention, the compounds of the formula I are administered in combination with nicotinic acid or niacin.

In one embodiment of the invention, the compounds of the formula I are administered in combination with a CETP inhibitor, e.g. CP-529, 414 (torcetrapib).

In one embodiment of the invention, the compounds of the formula I are administered in combination with an ACAT inhibitor.

In one embodiment of the invention, the compounds of the formula I are administered in combination with an MTP inhibitor such as, for example, implitapide.

In one embodiment of the invention, the compounds of the formula I are administered in combination with an antioxidant.

In one embodiment of the invention, the compounds of the formula I are administered in combination with a lipoprotein lipase inhibitor.

In one embodiment of the invention, the compounds of the formula I are administered in combination with an ATP citrate lyase inhibitor.

In one embodiment of the invention, the compounds of the formula I are administered in combination with a squalene synthetase inhibitor.

In one embodiment of the invention, the compounds of the formula I are administered in combination with a lipoprotein (a) antagonist.

Anti-obesity Agents

In one embodiment of the invention, the compounds of the formula I are administered in combination with a lipase inhibitor such as, for example, orlistat.

In one embodiment, the further active ingredient is fenfluramine or dexfenfluramine.

In another embodiment, the further active ingredient is sibutramine.

In a further embodiment, the compounds of the formula I are administered in combination with CART modulators (see "*Cocaine-Amphetamine-Regulated Transcript Influences Energy Metabolism, Anxiety and Gastric Emptying in Mice*" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl]-cyclohexyl-methyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexyl-ethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotonergic and noradrenergic compounds (e.g. WO00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tert-butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (Bromocriptine, Doprexin), lipase/amylase inhibitors (e.g. WO 00/40569), PPAR modulators (e.g. WO 00/78312), RXR modulators or TR-β agonists).

In one embodiment of the invention, the further active ingredient is leptin.

In one embodiment, the further active ingredient is dexamphetamine, amphetamine, mazindole or phentermine.

In one embodiment, the compounds of the formula I are as administered in combination with medicaments having effects on the coronary circulation and the vascular system, such as, for example, ACE inhibitors (e.g. ramipril), medicaments which act on the angiotensin-renin system, calcium antagonists, beta blockers etc.

In one embodiment, the compounds of the formula I are administered in combination with medicaments having an anti-inflammatory effect.

In one embodiment, the compounds of the formula are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention. The examples detailed below are provided to better describe and more specifically set forth the compounds, processes and methods of the present invention. It is to be recognized that they are for illustrative purposes only however, and should not be interpreted as limiting the spirit and scope of the invention as later recited by the claims that follow

EXAMPLES

Background

The activity of the compounds was tested as follows:

Determination of EC50 Values of PPAR Agonists in the Cellular PPARalpha Assay

Principle

The potency of substances which bind to human PPARalpha and activate it in an agonistic manner is analyzed using a stably transfected HEK cell line (HEK=human embryo kidney) which is referred to here as PPARalpha reporter cell line. It contains two genetic elements, a luciferase reporter element (pdeltaM-GAL4-Luc-Zeo) and a PPARalpha fusion protein (GR-GAL4-humanPPARalpha-LBD) which mediates expression of the luciferase reporter element depending on a PPARalpha ligand. The stably and constitutively expressed fusion protein GR-GAL4-humanPPARalpha-LBD binds in the cell nucleus of the PPARalpha reporter cell line via the GAL4 protein portion to the GAL4 DNA binding motifs 5'-upstream of the luciferase reporter element which is stably integrated in the genome of the cell line. There is only little expression of the luciferase reporter gene without addition of a PPARalpha ligand if fatty acid-depleted fetal calf serum (cs-FCS) is used in the assay. PPARalpha ligands bind and activate the PPARalpha fusion protein and thereby bring about expression of the luciferase reporter gene. The luciferase which is formed can be detected by means of chemiluminescence via an appropriate substrate.

Construction of the Cell Line

The PPARalpha reporter cell line was prepared in two steps. Firstly, the luciferase reporter element was constructed and stably transfected into HEK cells. For this purpose, five binding sites of the yeast transcription factor GAL4 (in each case 5'-CGGAGTACTGTCCTCCGAG-3') were cloned in 5'-upstream of a 68 bp-long minimal MMTV promoter (Genbank Accession # V01175). The minimal MMTV promoter section contains a CCAAT box and a TATA element in order to enable efficient transcription by RNA polymerase II. The cloning and sequencing of the GAL4-MMTV construct took place in analogy to the description of Sambrook J. et. al. (Molecular cloning, Cold Spring Harbor Laboratory Press, 1989). Then the complete *Photinus pyralis* luciferase gene (Genbank Accession # M15077) was cloned in 3'-downstream of the GAL4-MMTV element. After sequencing, the luciferase reporter element consisting of five GAL4 binding sites, MMTV promoter and luciferase gene was subcloned into a plasmid which confers zeozin resistance in order to obtain the plasmid pdeltaM-GAL4-Luc-Zeo. This vector was transfected into HEK cells in accordance with the statements in Ausubel, F. M. et al. (Current protocols in molecular biology, Vol. 1-3, John Wiley & Sons, Inc., 1995). Then zeozin-containing medium (0.5 mg/ml) was used to select a suitable stable cell clone which showed very low basal expression of the luciferase gene.

In a second step, the PPARalpha fusion protein (GR-GAL4-humanPPARalpha-LBD) was introduced into the stable cell clone described. For this purpose, initially the cDNA coding for the N-terminal 76 amino acids of the glucocorticoid receptor (Genbank Accession # P04150) was linked to the cDNA section coding for amino acids 1-147 of the yeast transcription factor GAL4 (Genbank Accession # P04386). The cDNA of the ligand-binding domain of the human PPARalpha receptor (amino acids S167-Y468; Genbank Accession # S74349) was cloned in at the 3' end of this GR-GAL4 construct. The fusion construct prepared in this way (GR-GAL4-humanPPARalpha-LBD) was subcloned into the plasmid pcDNA3 (from Invitrogen) in order to enable constitutive expression therein by the cytomegalovirus promoter. This plasmid was linearized with a restriction endonuclease and stably transfected into the previously described cell clone containing the luciferase reporter element. The finished PPARalpha reporter cell line which contains a luciferase reporter element and constitutively expresses the PPARalpha fusion protein (GR-GAL4-humanPPARalpha-LBD) was isolated by selection with zeozin (0.5 mg/ml) and G418 (0.5 mg/ml).

Assay Procedure

The activity of PPARalpha agonists is determined in a 3-day assay which is described below:

Day 1

The PPARalpha reporter cell line is cultivated to 80% confluence in DMEM medium (#41965-039, Invitrogen) which is mixed with the following additions: 10% cs-FCS (fetal calf serum; # SH-30068.03, Hyclone), 0.5 mg/ml zeozin (# R250-01, invitrogen), 0.5 mg/ml G418 (#10131-027, Invitrogen), 1% penicillin-streptomycin solution (#15140-122, Invitrogen) and 2 mM L-glutamine (#25030-024, invitrogen). The cultivation takes place in standard cell culture bottles (#353112, Becton Dickinson) in a cell culture incubator at 37° C. in the presence of 5% $CO_2$. The 80%-confluent cells are washed once with 15 ml of PBS (#14190-094, Invitrogen), treated with 3 ml of trypsin solution (#25300-054, Invitrogen) at 37° C. for 2 min, taken up in 5 ml of the DMEM medium described and counted in a cell counter. After dilution to 500 000 cells/ml, 35 000 cells are seeded in each well of a 96-well microtiter plate with a clear plastic base (#3610, Corning Costar). The plates are incubated in a cell culture incubator at 37° C. and 5% $CO_2$ for 24 h.

Day2

PPARalpha agonists to be tested are dissolved in DMSO in a concentration of 10 mM. This stock solution is diluted in DMEM medium (#41965-039, Invitrogen) which is mixed with 5% cs-FCS (# SH-30068.03, Hyclone), 2 mM L-glutamine (#25030-024, Invitrogen) and the previously described antibiotics (zeozin, G418, penicillin and streptomycin).

Test substances are tested in 11 different concentrations in the range from 10 µM to 100 pM. More potent compounds are tested in concentration ranges from 1 µM to 10 pM or between 100 nM and 1 pM.

The medium of the PPARalpha reporter cell line seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96-well microtiter plate. The DMSO concentration in the assay is less than 0.1% v/v in order to avoid cytotoxic effects of the solvent.

Each plate was charged with a standard PPARalpha agonist, which was likewise diluted in 11 different concentrations, in order to demonstrate the functioning of the assay in each individual plate. The assay plates are incubated in an incubator at 37° C. and 5% $CO_2$ for 24 h.

Day 3

The PPARalpha reporter cells treated with the test substances are removed from the incubator, and the medium is aspirated off. The cells are lyzed by pipetting 50 µl of Bright Glo reagent (from Promega) into each well of a 96-well microtiter plate. After incubation at room temperature in the dark for 10 minutes, the microtiter plates are measured in the luminometer (Trilux from Wallac). The measuring time for each well of a microtiter plate is 1 sec.

Evaluation

The raw data from the luminometer are transferred into a Microsoft Excel file. Dose-effect plots and EC50 values of PPAR agonists are calculated using the XL.Fit program as specified by the manufacturer (IDBS).

Determination of EC50 Values of PPAR Agonists in the Cellular PPARgamma Assay

Principle

A transient transfection system is employed to determine the cellular PPARgamma activity of PPAR agonists. It is based on the use of a luciferase reporter plasmid (pGL3basic-5×GAL4-TK) and of a PPARgamma expression plasmid (pcDNA3-GAL4-humanPPARgammaLBD). Both plasmids are transiently transfected into human mbryonic kidney cells (HEK cells). There is then expression in these cells of the usion protein GAL4-humanPPARgammaLBD which binds to the GAL4 binding sites of he reporter plasmid. In the presence of a PPARgamma-active ligand, the activated usion protein GAL4-humanPPARgammaLBD induces expression of the luciferase reporter gene, which can be detected in the form of a chemiluminescence signal after addition of a luciferase substrate. As a difference from the stably transfected PPARalpha reporter cell line, in the cellular PPARgamma assay the two components (luciferase reporter plasmid and PPARgamma expression plasmid) are transiently transfected into HEK cells because stable and permanent expression of the PPARgamma fusion protein is cytotoxic.

Construction of the Plasmids

The luciferase reporter plasmid pGL3basic-5×GAL4-TK is based on the vector pGL3basic from Promega. The reporter plasmid is prepared by cloning five binding sites of the yeast transcription factor GAL4 (each binding site with the sequence 5'-CTCGGAGGACAGTACTCCG-3'), together with a 160 bp-long thymidine kinase promoter section (Genbank Accession # AF027128) 5'-upstream into pGL3basic. 3'-downstream of the thymidine kinase promoter is the complete luciferase gene from *Photinus pyralis* (Genbank Accession # M15077), which is already a constituent of the plasmid pGL3basic used. The cloning and sequencing of the reporter plasmid pGL3basic-5×GAL4-TK took place in analogy to the description in Sambrook J. et. al. (Molecular cloning, Cold Spring Harbor Laboratory Press, 1989).

The PPARgamma expression plasmid pcDNA3-GAL4-humanPPARgammaLBD was prepared by first cloning the cDNA coding for amino acids 1-147 of the yeast transcription factor GAL4 (Genbank Accession # P04386) into the plasmid pcDNA3 (from Invitrogen) 3'-downstream of the cytomegalovirus promoter. Subsequently, the cDNA of the ligand-binding domain (LBD) of the human PPARgamma receptor (amino acids 1152-Y475; Accession # g1480099) 3'-downstream of the GAL4 DNA binding domain was cloned. Cloning and sequencing of the PPARgamma expression plasmid pcDNA3-GAL4-humanPPARgammaLBD again took place in analogy to the description in Sambrook J. et. al. (Molecular cloning, Cold Spring Harbor Laboratory Press, 1989). Besides the luciferase reporter plasmid pGL3basic-5×GAL4-TK and the PPARgamma expression plasmid pcDNA3-GAL4-humanPPARgammaLBD, also used for the cellular PPARgamma assay are the reference plasmid pRL-CMV (from Promega) and the plasmid pBluescript SK(+) from Stratagene. All four plasmids were prepared using a plasmid preparation kit from Qiagen, which ensured a plasmid quality with a minimal endotoxin content, before transfection into HEK cells.

Assay Procedure

The activity of PPARgamma agonists is determined in a 4-day assay which is described below. Before the transfection, HEK cells are cultivated in DMEM medium (#41965-039, Invitrogen) which is mixed with the following additions: 10% FCS (#16000-044, Invitrogen), 1% penicillin-streptomycin solution (#15140-122, Invitrogen) and 2 mM L-glutamine (#25030-024, Invitrogen).

Day 1

Firstly, solution A, a transfection mixture which contains all four plasmids previously described in addition to DMEM medium, is prepared. The following amounts are used to make up 3 ml of solution A for each 96-well microtiter plate for an assay: 2622 µl of antibiotic- and serum-free DMEM medium (#41965-039, Invitrogen), 100 µl of reference plasmid pRL-CMV (1 ng/µl), 100 µl of luciferase reporter plasmid pGL3basic-5×GAL4-TK (10 ng/µl), 100 µl of PPARgamma expression plasmid pcDNA3-GAL4-humanPPARgammaLBD (100 ng/µl) and 78 µl of plasmid pBluescript SK(+) (500 ng/µpl). Then 2 ml of solution B are prepared by mixing 1.9 ml of DMEM medium (#41965-039, Invitrogen) with 100 µl of PolyFect transfection reagent (from Qiagen) for each 96-well microtiter plate. Subsequently, 3 ml of solution A are mixed with 2 ml of solution B to give 5 ml of solution C, which is thoroughly mixed by multiple pipetting and incubated at room temperature for 10 min.

80%-confluent HEK cells from a cell culture bottle with a capacity of 175 cm² are washed once with 15 ml of PBS (#14190-094, Invitrogen) and treated with 3 ml of trypsin solution (#25300-054, Invitrogen) at 37° C. for 2 min. The cells are then taken up in 15 ml of DMEM medium (#41965-039, Invitrogen) which is mixed with 10% FCS (#16000-044, Invitrogen), 1% penicillin-streptomycin solution (#15140-122, invitrogen) and 2 mM L-glutamine (#25030-024, Invitrogen). After the cell suspension has been counted in a cell counter, the suspension is diluted to 250 000 cells/ml. 15 ml of this cell suspension are mixed with 5 ml of solution C for one microtiter plate. 200 µl of the suspension are seeded in each well of a 96-well microtiter plate with a clear plastic base (#3610, Corning Costar). The plates are incubated in a cell culture incubator at 37° C. and 5% CO₂ for 24 h.

Day 2

PPAR agonists to be tested are dissolved in DMSO in a concentration of 10 mM. This stock solution is diluted in DMEM medium (#41965-039, Invitrogen) which is mixed with 2% Ultroser (#12039-012, Biosepra), 1% penicillin-streptomycin solution (#15140-122, Invitrogen) and 2 mM L-glutamine (#25030-024, Invitrogen). Test substances are tested in a total of 11 different concentrations in the range from 10 µM to 100 pM. More potent compounds are tested in concentration ranges from 1 µM to 10 pM.

The medium of the HEK cells transfected and seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96-well microtiter plate. Each plate is charged with a standard PPARgamma agonist, which is likewise diluted in 11 different concentrations, in order to demonstrate the functioning of the assay in each individual plate. The assay plates are incubated in an incubator at 37° C. and 5% CO₂ for 48 h.

Day 4

After removal of the medium by aspiration, 50 µl of Dual-Glo™ reagent (Dual-Glo™ Luciferase Assay System; Promega) are added to each well in accordance with the manufacturer's instructions in order to lyze the cells and provide the substrate for the firefly luciferase (*Photinus pyralis*) formed in the cells. After incubation at room temperature in the dark for 10 minutes, the firefly luciferase-mediated chemiluminescence is measured in a measuring instrument (measuring time/well 1 sec; Trilux from Wallac). Then 50 µl of the Dual-Glo™ Stop & Glo reagent (Dual-Glo™ Luciferase Assay System; Promega) is added to each well in order to stop the activity of the firefly luciferase and provide the substrate for the Renilla luciferase expressed by the reference plasmid pRL-CMV. After incubation at room temperature in the dark for a further 10 minutes, the chemiluminescence mediated by the Renilla luciferase is again measured for 1 sec/well in the measuring instrument.

Evaluation

The raw data from the luminometer are transferred into a Microsoft Excel file. The firefly/Renilla luciferase activity ratio is determined for each measurement derived from one well of the microtiter plate. The dose-effect plots and EC50 values of PPAR agonists are calculated from the ratios by the XL.Fit program as specified by the manufacturer (IDBS).

The results for the activity of some compounds of the invention of the formula I are indicated in Table I below:

TABLE I

| Example No. | Formula | EC50 PPARalpha [µM] | EC50 PPARgamma [µM] |
|---|---|---|---|
| 1 | | 0.045 | 0.93 |
| 2 | | 0.0035 | 2.9 |
| 3 | | 0.019 | 0.67 |
| 4 | | 0.0020 | 1.1 |
| 5 | | 0.012 | 1.5 |
| 7 | | 0.0012 | 2.6 |
| 9 | | 0.32 | 0.39 |
| 10 | | 0.054 | 0.13 |
| 11 | | 0.0041 | 0.87 |
| 12 | | 0.012 | 0.075 |
| 13 | | 0.0066 | 0.13 |
| 14 | | 0.00038 | 0.22 |
| 14 | | 0.00053 | 0.056 |
| 15 | | 0.00039 | 0.16 |

TABLE I-continued

| Example No. | Formula | EC50 PPARalpha [μM] | EC50 PPARgamma [μM] |
|---|---|---|---|
| 16 | | 0.017 | 0.40 |
| 17 | | 0.00016 | 0.51 |
| 18 | | 0.0026 | 0.15 |
| 19 | | 0.00038 | 0.54 |
| 20 | | 0.00054 | 0.17 |
| 21 | | 0.0058 | 0.60 |
| * | | 0.0018 | >10 000 |
| ** | cis/racemate | 0.0045 | >10 000 |

* Example 8a from WO 2004/076427.
** Example 10 from WO 2004/076427.

It is evident from Table I that the compounds of the invention of the formula I activate the PPARalpha receptor and the PPARgamma receptor and thus for example bring about a lowering of triglycerides in the body in analogy to fibrates in clinical use (see, for example, J.-Ch. Fruchard et al.,: PPARS, Metabolic Disease and Atherosclerosis, Pharmacological Research, Vol. 44, No. 5, 2001; S. Kersten et al.: Roles of PPARs in health and disease, NATURE, VOL 405, 25 MAY 2000; I. Pineda et al.: Peroxisome proliferator-activated receptors: from transcriptional control to clinical practice, Curr Opin Lipidol 12: 2001,245-254).

TABLE II

| Ex. | R1 | R2 | R3 | R4 | R5 |
|---|---|---|---|---|---|
| 1 | H | 3-OCH3 | C2H5 | CH3 | H |
| 2 | 4-CH3 | H | C2H5 | CH3 | H |
| 3 | 4-i-C4H9 | H | C2H5 | CH3 | H |
| 4 | 2-Naphthyl | | C2H5 | CH3 | H |
| 5 | H | 3-CF3 | C2H5 | CH3 | H |
| 6 | 4-i-C3H7 | H | C2H5 | CH3 | H |
| 7 | 2-Naphthyl | | CH3 | CH3 | H |
| 8[a] | H | 3-OCH3 | i-C3H7 | CH3 | H |
| 9 | H | 3-OCH3 | i-C3H7 | CH3 | H |
| 10 | H | 3-OCH3 | C2H5 | n-C3H7 | H |
| 11 | 4-CH3 | H | C2H5 | n-C3H7 | H |
| 12 | 4-i-C4H9 | H | C2H5 | n-C3H7 | H |
| 13 | 2-Naphthyl | | C2H5 | n-C3H7 | H |
| 14 | 4-i-C3H7 | H | C2H5 | n-C3H7 | H |
| 15 | 2-Naphthyl | | CH3 | n-C3H7 | H |
| 16 | H | 3-OCH3 | C2H5 | CH2Ph | H |
| 17 | 4-CH3 | H | C2H5 | CH2Ph | H |
| 18 | 4-i-C4H9 | H | C2H5 | CH2Ph | H |
| 19 | 2-Naphthyl | | C2H5 | CH2Ph | H |
| 20 | 4-i-C3H7 | H | C2H5 | CH2Ph | H |
| 21 | 2-Naphthyl | | CH3 | CH2Ph | H |

[a] racemate

Processes

The compounds of the invention of the formula I can be obtained in accordance with the following reaction schemes:

Process A:

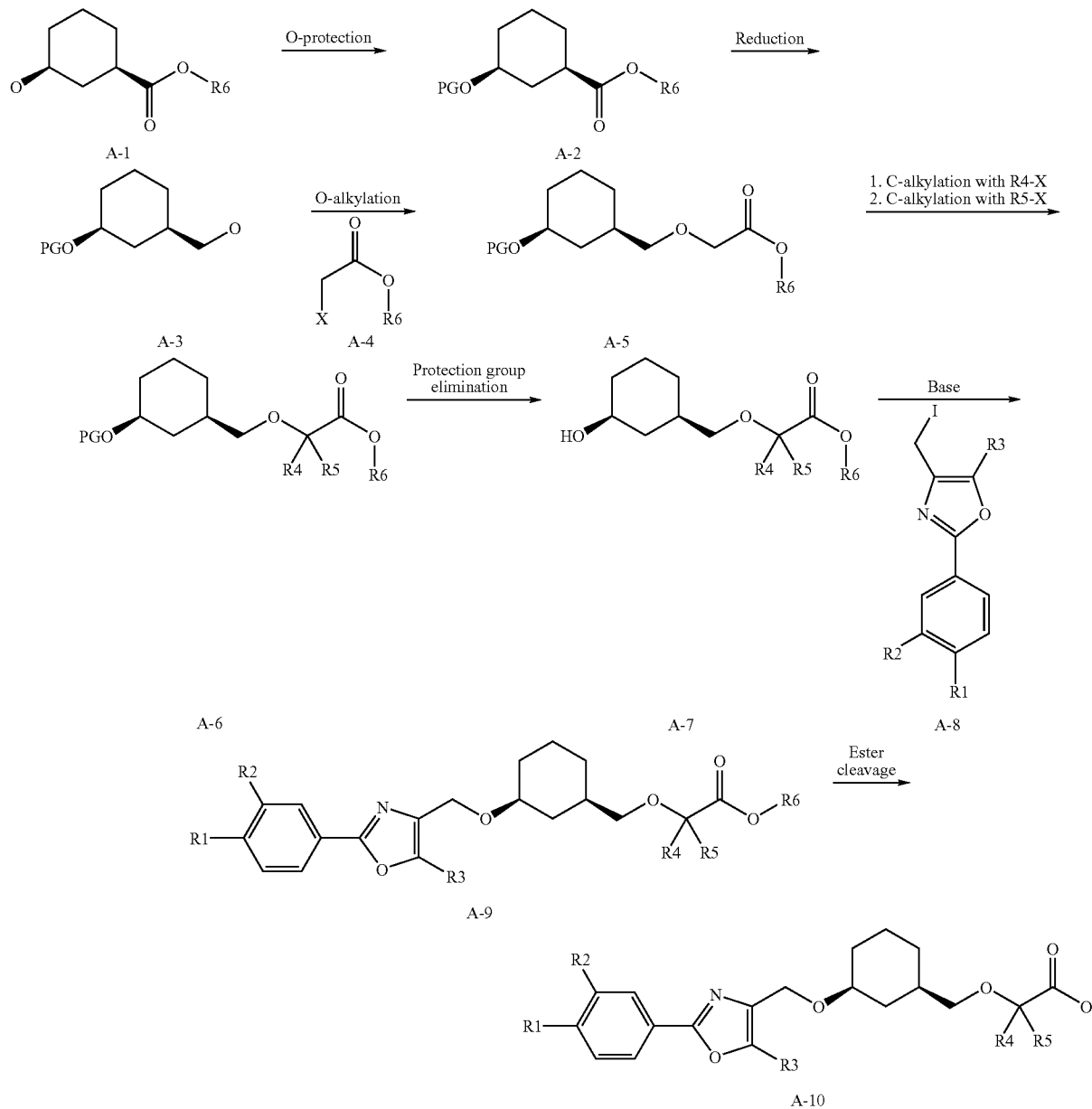

The compound A-1 is protected on the secondary hydroxyl group (for example for PG=TBDPS; by stirring with TBDP-SCI and imidazole in DMF at RT or for PG=THP; by stirring with dihydropyran and toluenesulfonic acid in dichloromethane at RT), resulting in the compound A-2, in which R6 has the meaning described above. A-2 is reduced with lithium aluminum hydride in an etheral solvent to the compound A-3. The compound A-3 is reacted with the compound A-4—an ester of 2-haloacetic acid and of the alcohol R6-OH in which R6 has the meaning described above and halogen can be chlorine, bromine or iodine—to give the compound A-5. The compound A-5 is reacted with a lithium amide base (e.g. lithium diisopropylamide or lithium-2,2,5,5-tetramethylpyrrolidide) and an alkyl halide of the general formula R4X, in which R4 has the meaning described above and halogen can be chlorine, bromine or iodine, in an etheral solvent at low temperature. The compound obtained in this way is then reacted with a lithium amide base (e.g. lithium diisopropylamide or lithium-2,2,5,5-tetramethylpyrrolidide) and an alkyl halide of the general formula R5X, in which R5 has the meaning described above and halogen can be chlorine, bromine or iodine, in an etheral solvent at low temperature to give the compound A-6. The protective group is eliminated from A-6 (in the case of PG=TBDPS with tetrabutylammonium fluoride in THF or in the case of PG=THP with toluenesulfonic acid in methanol), resulting in the compound of the general formula A-7. The compound A-7 is reacted with a base (for example sodium hydride or potassium tert-butoxide) and the compound A-8 (see Process A) in which R1, R2 and R3 have the meanings described above in an etheral solvent to give the compound A-9. The compound A-9 is hydrolyzed to the acid A-10: in the case where R6 are primary or secondary alkyl radicals, with a base in methanol, or in the case where R6 is a tertiary alkyl radical, with anhydrous acid in an inert solvent (for example hydrogen chloride in dioxane or trifluoroacetic acid in dichloromethane).

Enantiomerically pure compounds are synthesized starting from the enantiomerically pure ester A-1.

Examples 1 to 21 can be synthesized by this process.

The abbreviations used stand for:

| | |
|---|---|
| Ac | Acetyl |
| Bn | Benzyl |
| Bu | Butyl |
| iBu | Isobutyl |
| tBu | tert-Butyl |
| BuLi | n-Butyllithium |
| Bz | Benzoyl |
| Cy | Cyclohexyl |
| DCI | Direct chemical ionization (in MS) |
| DCM | Dichloromethane |
| DHP | 2,3-Dihydropyran |
| DMAP | 4-N,N-Dimethylaminopyridine |
| DMF | N,N-Dimethylformamide |
| DMSO | Dimethyl sulfoxide |
| EA | Ethyl acetate |
| EDC | N'-(3-Dimethylaminopropyl)-N-ethylcarbodiimide × HCl |
| EI | Electron impact ionization (in MS) |
| equiv. | Equivalent |
| ESI | Electron spray ionization (in MS) |
| Et | Ethyl |
| h | Hour |
| HATU | O-(7-Azabenzotriazol-1-yl)-N,N,N',N'-tetramethyluronium hexafluorophosphate |
| HOBt | 1-Hydroxy-1H-benzotriazole × H2O |
| HPLC | High pressure, high performance liquid chromatography |
| LC-MS | Coupled liquid chromatography-mass spectroscopy |
| Me | Methyl |
| MS | Mass spectroscopy |
| MsCl | Methanesulfonyl chloride |
| MTBE | tert-Butyl methyl ether |
| NMR | Nuclear magnetic resonance spectroscopy |
| Pd/C | Palladium on carbon |
| Ph | Phenyl |
| iPr | Isopropyl |
| nPr | n-Propyl |
| Rf | Retention ratio (in TLC) |
| RT | Room temperature |
| sat. | Saturated |
| TBAF | Tetrabutylammonium fluoride |
| TBAI | Tetrabutylammonium iodide |
| TBDPSCI | tert-Butyldiphenylsilyl chloride |
| TBDMSCI | tert-Butyldimethylsilyl chloride |
| TFA | Trifluoroacetic acid |
| THF | Tetrahydrofuran |
| THP | Tetrahydropyranyl |
| TLC | Thin layer chromatography |
| Tr | Trityl |
| TsOH | Toluene sulfonic acid |

Other compounds can be prepared in accordance with the abovementioned processes.

Building block synthesis of the compounds of the general formula A-8:

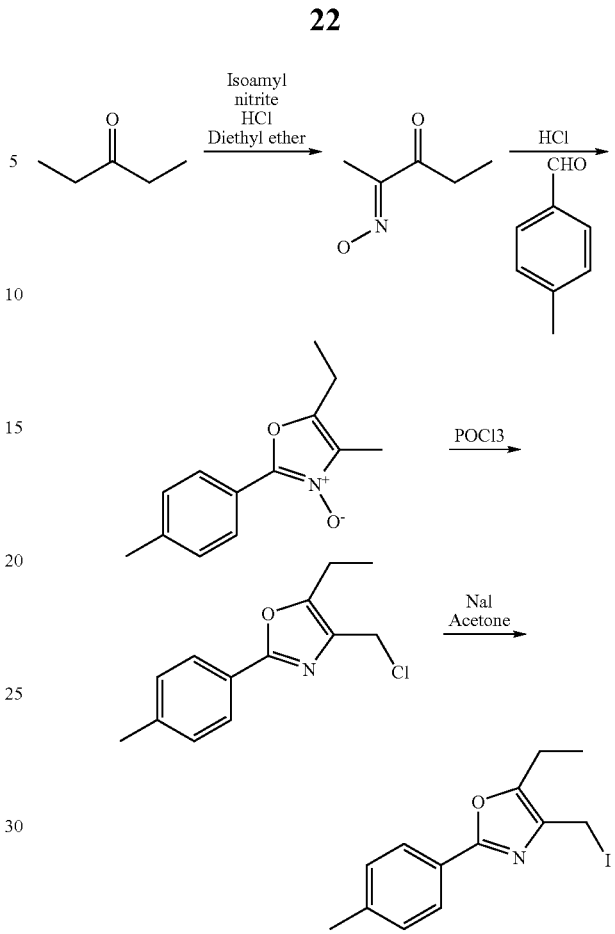

Diethyl ketone is reacted with isoamyl nitrite and HCl in diethyl ether, resulting in pentane-2,3-dione 2-oxime (G. Buechi, J. Galindo, J.Org.Chem. (1991) 56(8), 2605-2606). The latter is reacted with p-methylbenzaldehyde and HCl in acetic acid to give 5-ethyl-4-methyl-2-p-tolyloxazole 3-oxide (P. M. Weintraub, J. Med. Chem. (1972) 15(4), 419-420). Boiling this compound with phosphoryl chloride in chloroform results in 4-chloromethyl-5-ethyl-2-p-tolyloxazole (M. S. Malamas, R. P. Carlson, D. Grimes, R. Howell, K. Glaser, I. Gunawan, J. A. Nelson, M. Kanzelberger, U. Shah, D. A. Hartman, J. Med. Chem. (1996) 39(1), 237-245). This compound is heated with sodium iodide in acetone under reflux, resulting in 5-ethyl-4-iodomethyl-2-p-tolyloxazole (A., Zlatkov, P., Peikov, J., Rodriguez-Alvarez, N., Danchev, I., Nikolova, J., Mitkov, Eur.J.Med.Chem.Chim.Ther. (2000) 35(10), 941-948).

The following building blocks are obtained in analogy to the synthesis from the precursors depicted in Table III:

TABLE III

| No. | Ketone (Precursor 1) | Aldehyde (Precursor 2) | Product |
|---|---|---|---|
| 1 | ![ketone] | ![aldehyde] | ![product] |

TABLE III-continued

| No. | Ketone (Precursor 1) | Aldehyde (Precursor 2) | Product |
|---|---|---|---|
| 2 | pentan-3-one | 4-methylbenzaldehyde | 5-ethyl-4-(iodomethyl)-2-(p-tolyl)oxazole |
| 3 | pentan-3-one | 4-isobutylbenzaldehyde | 5-ethyl-4-(iodomethyl)-2-(4-isobutylphenyl)oxazole |
| 4 | pentan-3-one | 2-naphthaldehyde | 5-ethyl-4-(iodomethyl)-2-(naphthalen-2-yl)oxazole |
| 5 | pentan-3-one | 3-(trifluoromethyl)benzaldehyde | 5-ethyl-4-(iodomethyl)-2-(3-(trifluoromethyl)phenyl)oxazole |
| 6 | pentan-3-one | 4-isopropylbenzaldehyde | 5-ethyl-4-(iodomethyl)-2-(4-isopropylphenyl)oxazole |
| 7 | butan-2-one | 2-naphthaldehyde | 4-(iodomethyl)-5-methyl-2-(naphthalen-2-yl)oxazole |
| 8 | 2-methylpentan-3-one | 3-methoxybenzaldehyde | 4-(iodomethyl)-5-isopropyl-2-(3-methoxyphenyl)oxazole |

Example 1

2-{(1R,3S)-3-[5-Ethyl-2-(4-methoxyphenyl)-oxazol-4-ylmethoxy]cyclohexylmethoxy}-2-methylpropionic acid

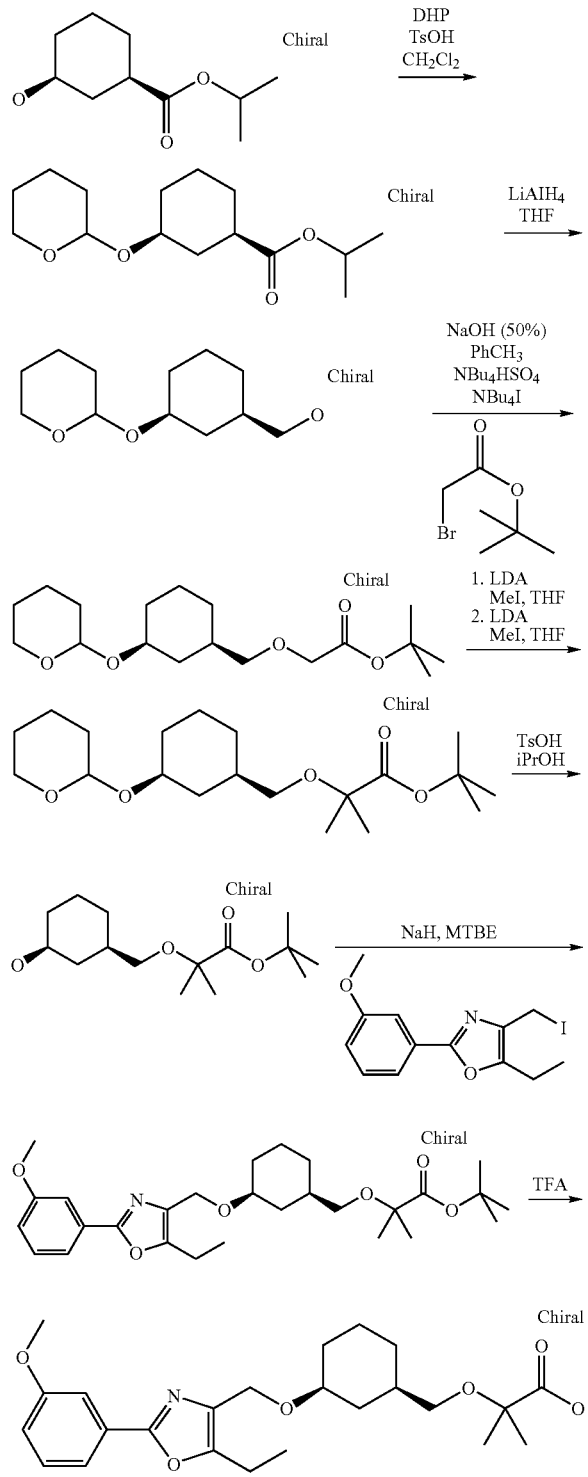

Isopropyl (1R,3S)-3-(tetrahydropyran-2-yloxy)cyclohexanecarboxylate

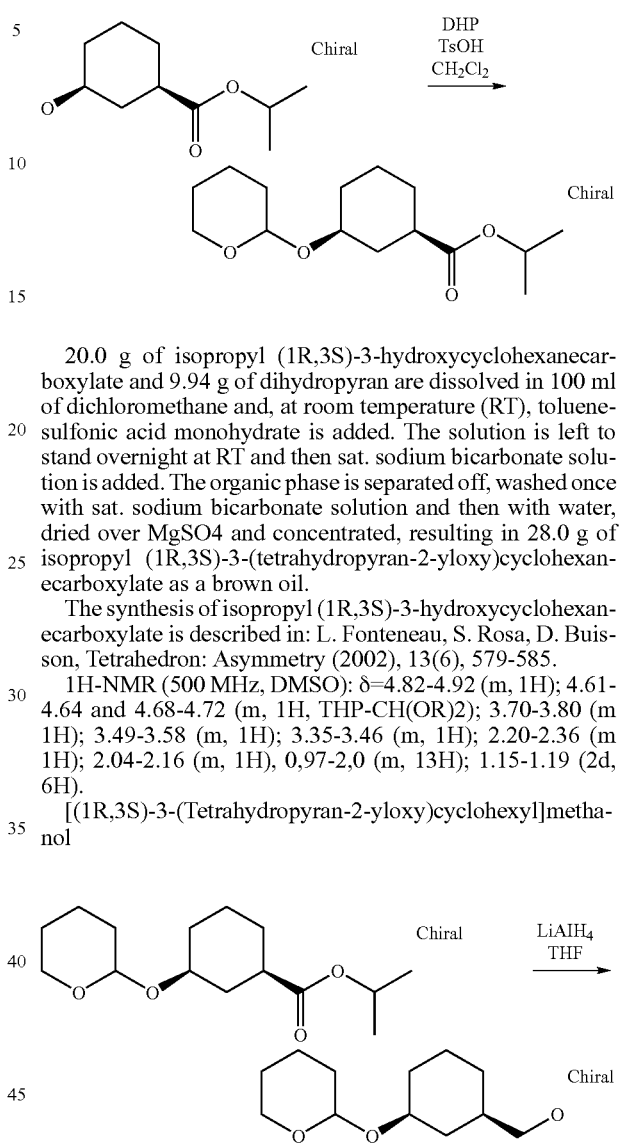

20.0 g of isopropyl (1R,3S)-3-hydroxycyclohexanecarboxylate and 9.94 g of dihydropyran are dissolved in 100 ml of dichloromethane and, at room temperature (RT), toluenesulfonic acid monohydrate is added. The solution is left to stand overnight at RT and then sat. sodium bicarbonate solution is added. The organic phase is separated off, washed once with sat. sodium bicarbonate solution and then with water, dried over MgSO4 and concentrated, resulting in 28.0 g of isopropyl (1R,3S)-3-(tetrahydropyran-2-yloxy)cyclohexanecarboxylate as a brown oil.

The synthesis of isopropyl (1R,3S)-3-hydroxycyclohexanecarboxylate is described in: L. Fonteneau, S. Rosa, D. Buisson, Tetrahedron: Asymmetry (2002), 13(6), 579-585.

1H-NMR (500 MHz, DMSO): δ=4.82-4.92 (m, 1H); 4.61-4.64 and 4.68-4.72 (m, 1H, THP-CH(OR)2); 3.70-3.80 (m 1H); 3.49-3.58 (m, 1H); 3.35-3.46 (m, 1H); 2.20-2.36 (m 1H); 2.04-2.16 (m, 1H), 0,97-2,0 (m, 13H); 1.15-1.19 (2d, 6H).

[(1R,3S)-3-(Tetrahydropyran-2-yloxy)cyclohexyl]methanol 47 g of isopropyl (1R,3S)-3-(tetrahydropyran-2-yloxy)cyclohexanecarboxylate are, at 0° C., added dropwise to a suspension of 13.2 g of lithium aluminum hydride in THF. The mixture is stirred at RT for 1 h, then, at 0° C., 68 ml of ethyl acetate and subsequently 55.6 g of sodium hydroxide, dissolved in 62.6 ml of water, are added.

Then 50 ml of methanol are added and the mixture is stirred until the precipitate is white. 50 g of magnesium sulfate are added to the suspension, which is then filtered. The filtrate is concentrated, whereupon further magnesium sulfate precipitates; it is completely precipitated with MTBE and filtered off. Removal of the solvent by distillation results in 34 g of [(1R, 3S)-3-tetrahydropyran-2-yloxy)cyclohexyl]methanol as pale yellow oil.

1H-NMR (500 MHz, DMSO): δ=4.67-4.72 (m, 1H); 4.36-4.42 (m, 1H); 3.73-3.8 (m, 1H); 3.44-3.52 (m, 1H); 3.37-3.44 (m, 1H); 3.16-3.27 (m, 2H); 1.84-2.04 (m 2H); 1.66-1.75 (m, 2H), 1.54-1.64 (m, 2H); 1.32-1.51 (m, 4h); 1.08-1.30 (m, 2H); 0.67-1.02 (m, 3H).

tert-Butyl [(1R, 3S)-3-(tetrahydropyran-2-yloxy)cyclohexylmethoxy]acetate

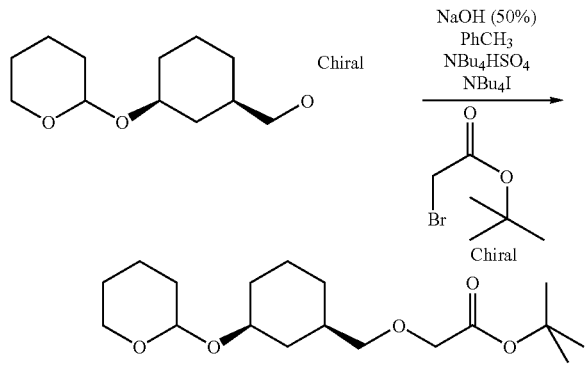

34 g of [(1R,3S)-3-(tetrahydropyran-2-yloxy)cyclohexyl]methanol, 100 g of tert-butyl bromoacetate, 16.2 g of tetrabutylammonium bisulfate and 5.9 g of tetrabutylammonium iodide are dissolved in 250 ml of toluene and, at 10° C. (ice-water bath), a solution of 63.5 g of sodium hydroxide in 80 ml of water is added, and the mixture is stirred vigorously (KPG paddle stirrer) at 10° C. for 8 h. Then MTBE and water are added, and the phases are separated. The aqueous phase is extracted twice with MTBE, and the combined organic phases are washed with saturated sodium chloride solution, dried over magnesium sulfate and concentrated. The residue is chromatographed on silica gel (heptane/ethyl acetate gradient). This results in 36.4 g of tert-butyl [(1R,3S)-3-(tetrahydropyran-2-yloxy)cyclohexylmethoxy]acetate and 6.8 g of [(1R,3S)-3-(tetrahydropyran-2-yloxy)cyclohexyl]methanol as pale yellow oils.

C18H32O5 (328.22); MS (Cl+): 329 (3) [MH$^+$], 245.2 (100) [MH$^+$—C5H8O], 189.2 (50) [MH$^+$—C5H8O—C4H8].

tert-Butyl 2-methyl-2-[(1R,3S)-3-(tetrahydropyran-2-yloxy)cyclohexylmethoxy]-propionate

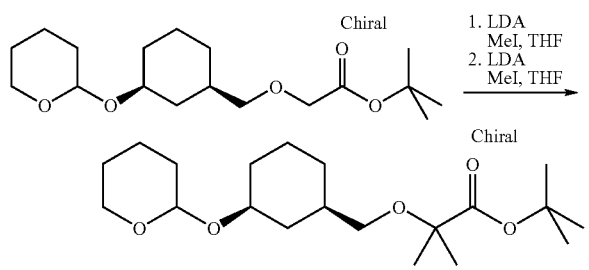

100 ml of a solution of lithium diisopropylamide (2M in THF) are added to a solution of 30 g of tert-butyl [(1R,3S)-3-(tetrahydropyran-2-yloxy)cyclohexylmethoxy]acetate in 250 ml of THF at −78° C., during which the temperature should not rise above −55° C. The solution is stirred at this temperature for 10 min and then warmed to −10° C. and stirred at this temperature for a further 15 min, after which the solution is again cooled to −78° C., and 17.1 ml of methyl iodide are added dropwise. The solution is warmed to −10° C. and then saturated ammonium chloride solution and MTBE are added. The phases are separated, the organic phase is washed with saturated ammonium chloride solution, the combined aqueous phases are extracted once more with MTBE, and then the combined organic phases are washed with saturated sodium chloride solution, dried over magnesium sulfate and concentrated.

87 ml of a solution of lithium diisopropylamide (2M in THF) are added to a solution of the residue obtained in this way in 217 ml of THF at −78° C., during which the temperature should not rise above −55° C. The solution is stirred at this temperature for 10 min and then warmed to −10° C. and stirred at this temperature for a further 15 min, after which the solution is again cooled to −78° C., and 14.7 ml of methyl iodide are added dropwise. The solution is warmed to −10° C. and then saturated ammonium chloride solution and MTBE are added. The phases are separated, the organic phase is washed with saturated ammonium chloride solution, the combined aqueous phases are extracted once more with MTBE, and then the combined organic phases are washed with saturated sodium chloride solution, dried over magnesium sulfate and concentrated, resulting in 29 g of tert-butyl 2-methyl-2-[(1R,3S)-3-(tetrahydropyran-2-yloxy)cyclohexylmethoxy]propionate as yellow oil.

1H-NMR (500 MHz, DMSO): □=4.68-4.72 (m, 1H); 3.74-3.80 (m, 1H); 3.44-3.53 (m, 1H); 3.38-3.44 (m, 1H); 3.13-3.17 (m, 1H); 3.06-3.12 (m, 1H); 1.70-2.06 (m, 2H); 0.73-1.76 (m, 13H); 1.42 (s, 9H); 1.27 (s, 6H).

tert-Butyl 2-((1R,3S)-3-hydroxycyclohexylmethoxy)-2-methylpropionate

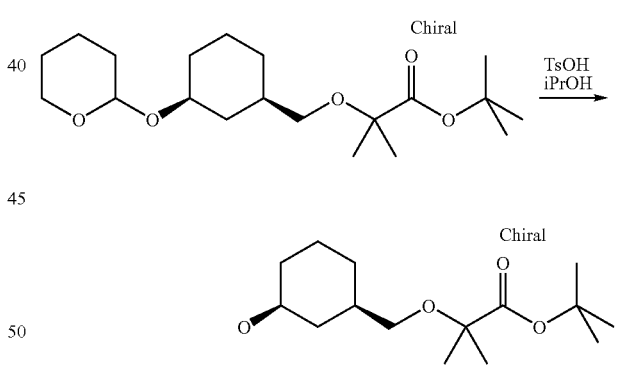

29 g of tert-butyl 2-methyl-2-[(1R,3S)-3-(tetrahydropyran-2-yloxy)cyclohexylmethoxy]-propionate are dissolved in 150 ml of isopropanol, and 2.3 g of toluenesulfonic acid monohydrate are added. After the toluenesulfonic acid has completely dissolved, the solution is left to stand for 4 days and then mixed with saturated sodium bicarbonate solution and partly concentrated. The residue is taken up MTBE/water, the phases are separated, the aqueous phase is extracted with MTBE, and the combined organic phases are dried over magnesium sulfate and concentrated. The residue is chromatographed on silica gel with heptane/ethyl acetate 3:1, resulting in 13.8 g of tert-butyl 2-((1R,3S)-3-hydroxycyclohexylmethoxy)-2-methylpropionate as yellow oil.

C15H28O4 (272.20); MS (CI+): 273.4 (24) [MH+], 217.2 (100) [MH+—C4H8], 199 (18), 113 (19).

tert-Butyl 2-{(1R ,3S)-3-[5-ethyl-2-(3-methoxyphenyl)oxazol-4-ylmethoxy]-cyclohexylmethoxy}-2-methylpropionate

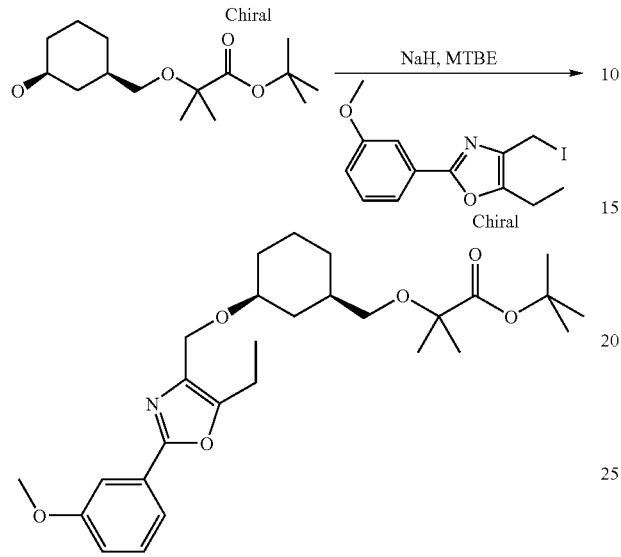

200 mg of tert-butyl 2-((1R,3S)-3-hydroxycyclohexylmethoxy)-2-methylpropionate are added dropwise as solution in MTBE to a suspension of 65 mg of sodium hydride (60% by weight in mineral oil) in 10 ml of MTBE. After gas evolution ceases, 503 mg of 4-iodomethyl-5-ethyl-2-(3-methoxyphenyl)oxazole are added as solution in MTBE, and the suspension is heated under reflux overnight. Ethyl acetate (MTBE can also be used) is added to the reaction mixture, and the mixture is washed with water and saturated sodium chloride solution, dried over magnesium sulfate and concentrated. The residue is chromatographed on silica gel (heptane/ethyl acetate gradient), resulting in 323 mg of tert-butyl 2-{(1R,3S)-3-[5-ethyl-2-(3-methoxyphenyl)oxazol-4-ylmethoxy]cyclohexylmethoxy}-2-methylpropionate as yellow oil.

C28H41 NO6 (487.64): LCMS (ESI): 488.41 [MH+].

2-{(1R,3S)-3-[5-ethyl-2-(3-methoxyphenyl)oxazol-4-ylmethoxy]cyclohexylmethoxy}-2-methylpropionic acid

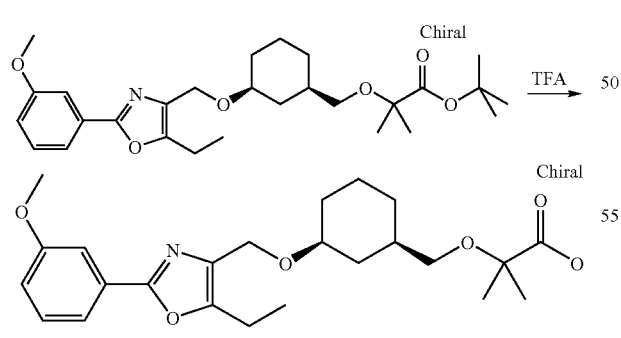

300 mg of tert-butyl 2-{(1R,3S)-3-[5-ethyl-2-(3-methoxyphenyl)oxazol-4-ylmethoxy]-cyclohexylmethoxy}-2-methylpropionate are left to stand in 1 ml of trifluoroacetic acid at RT overnight. The solution is completely evaporated, water is added to the residue, and the pH is adjusted to 3 with sodium bicarbonate solution. The solution is extracted with ethyl acetate, and the organic phase is washed twice with water, dried over magnesium sulfate and concentrated. The residue is chromatographed on silica gel (dichloromethane/methanol gradient), resulting in 256 mg of 2-{(1R,3S)-3-[5-ethyl-2-(3-methoxyphenyl)oxazol-4-ylmethoxy]cyclohexylmethoxy}-2-methylpropionic acid as yellow resin.

C24H33NO6 (431.53): LCMS (ESI): 432.1 [MH+].

Example 2

2-[(1R,3S)-3-(5-Ethyl-2-p-tolyloxazol-4-ylmethoxy)cyclohexylmethoxy]-2-methylpropionic acid

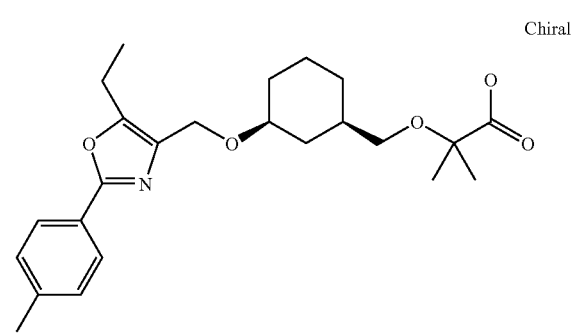

2-[(1R,3S)-3-(5-Ethyl-2-p-tolyloxazol-4-ylmethoxy)cyclohexylmethoxy]-2-methylpropionic acid is obtained in analogy to Example 1 from tert-butyl 2-((1R,3S)-3-hydroxycyclohexylmethoxy)-2-methylpropionate and 4-iodomethyl-5-ethyl-2-p-tolyloxazole.

C24H33NO5 (415.24): LCMS (ESI): 416.39 [MH+].

Example 3

2-{(1R,3S)-3-[5-Ethyl-2-(4-isobutylphenyl)-oxazol-4-ylmethoxy]cyclohexylmethoxy}-2-methylpropionic acid

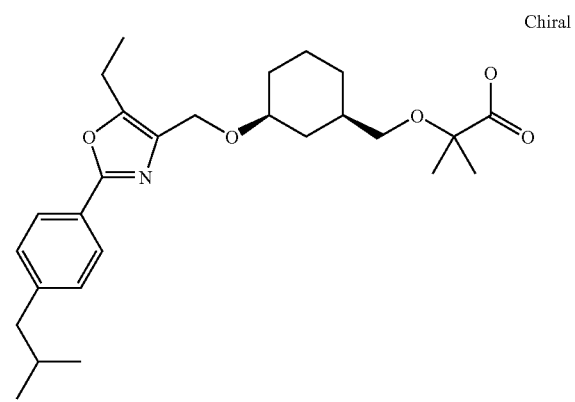

2-{(1R,3S)-3-[5-Ethyl-2-(4-isobutylphenyl)oxazol-4-ylmethoxy]cyclohexylmethoxyl}-2-methylpropionic acid is obtained in analogy to Example 1 from tert-butyl 2-((1R,3S)-3-hydroxycyclohexylmethoxy)-2-methylpropionate and 4-iodomethyl-5-ethyl-2-(4-isobutylphenyl)oxazole.

C27H39NO5 (457.28): LCMS (ESI): 458.43 [MH+].

Example 4

2-{(1R,3S)-3-[5-Ethyl-2-(napth-2-yl)oxazol-4-yl-methoxy]cyclohexylmethoxy}-2-methylpropionic acid

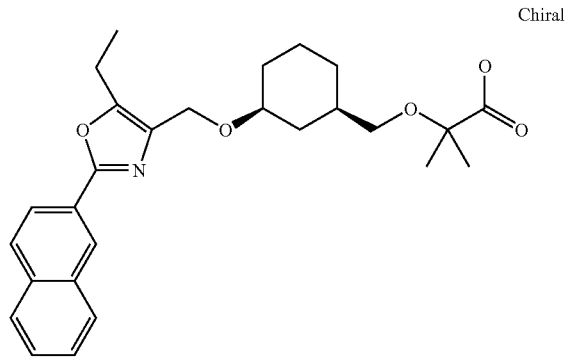

2-{(1R,3S)-3-[5-Ethyl-2-(naphth-2-yl)oxazol-4-yl-methoxy]cyclohexylmethoxy}-2-methylpropionic acid is obtained in analogy to Example 1 from tert-butyl 2-((1R,3S)-3-hydroxyclyclohexylmethoxy)-2-methylpropionate and 5-ethyl-4-iodomethyl-2-(naphthyl-2-yl)oxazole.

C27H33NO5 (451.24): LCMS (ESI): 452.19 [MH+].

Example 5

2-{(1R,3S)-3-[5-Ethyl-2-(3-trifluoromethylphenyl)oxazol-4-ylmethoxy]cyclo-hexylmethoxy}-2-methylpropionic acid

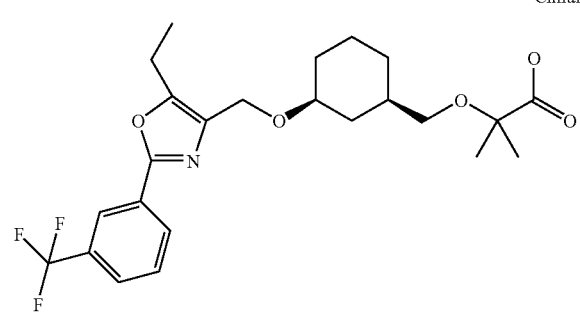

2-{(1R,3S)-3-[5-Ethyl-2-(3-trifluoromethylphenyl)oxazol-4-ylmethoxy]cyclo-hexylmethoxy}-2-methylpropionic acid is obtained in analogy to Example 1 from tert-butyl 2-((1R,3S)-3-hydroxycyclohexylmethoxy)-2-methylpropionate and 5-ethyl-4-iodomethyl-2-(3-trifluoromethylphenyl)oxazole.

C24H30F3NO5 (469.21): LCMS (ESI): 470.20 [MH+].

Example 6

2-{(1R 3S)-3-[5-Ethyl-2-(4-isopropylphenyl)oxazol-4-ylmethoxy]cyclohexylmethoxy}-2-methylpropionic acid

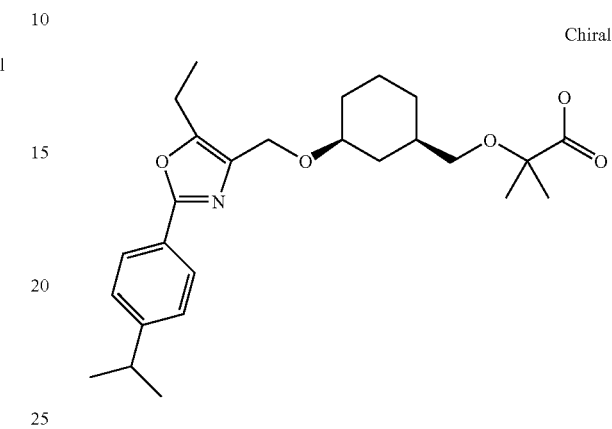

2-{(1R,3S)-3-[5-Ethyl-2-(4-isopropylphenyl)oxazol-4-ylmethoxy]cyclohexylmethoxy}-2-methylpropionic acid is obtained in analogy to Example 1 from tert-butyl 2-((1R,3S)-3-hydroxycyclohexylmethoxy)-2-methylpropionate and 5-ethyl-4-iodomethyl-2-(4-isopropylphenyl)oxazole.

C26H37NO5 (443.27): LCMS (ESI): 488.72 [M+HCOO].

Example 7

2-Methyl-2-{(1R,3S)-3-[5-methyl-2-(naphth-2-yl)oxazol-4-ylmethoxy]cyclo-hexylmethoxy}propionic acid

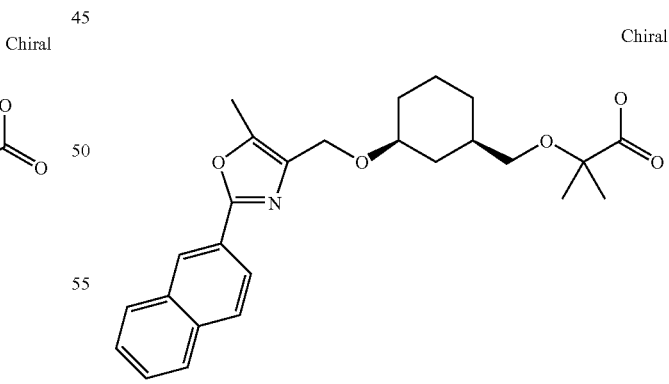

2-Methyl-2-{(1R,3S)-3-[5-methyl-2-(naphth-2-yl)oxazol-4-ylmethoxy]cyclo-hexylmethoxy}propionic acid is obtained in analogy to Example 1 from tert-butyl 2-((1R,3S)-3-hydroxycyclohexylmethoxy)-2-methylpropionate and 5-methyl-4-iodomethyl-2-(naphth-2-yl)oxazole.

C26H31NO5 (437.22): LCMS (ESI): 438.17 [MH+].

Example 8

2-{cis-3-[5-Isopropyl-2-(3-methoxyphenyl)oxazol-4-ylmethoxy]cyclohexylmethoxy}-2-methylpropionic acid

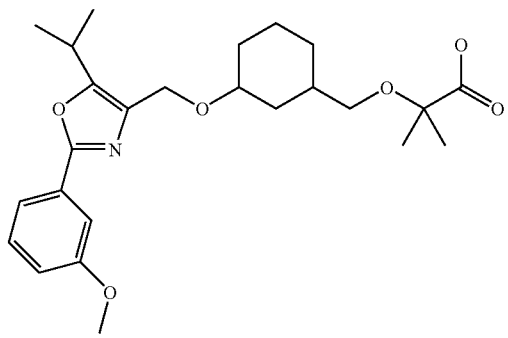

Racemic 2-{cis-3-[5-isopropyl-2-(3-methoxyphenyl)oxazol-4-ylmethoxy]cyclo-hexylmethoxy}-2-methylpropionic acid is obtained in analogy to Example 1 from racemic tert-butyl 2-(cis-3-hydroxycyclohexylmethoxy)-2-methylpropionate and 4-iodomethyl-2-(3-methoxyphenyl)-5-isopropyloxazole.

C25H35NO6 (445.25): LCMS (ESI): 446.27 [MH+].

Example 9

2-{(1R,3S)-3-[5-Isopropyl-2-(3-methoxypheny)oxazol-4-ylmethoxy]cyclo-hexylmethoxy}-2-methyl propionic acid Chiral

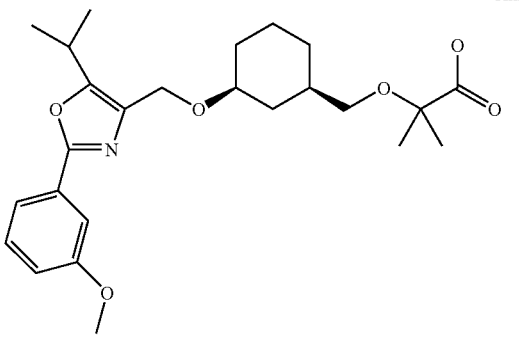

2-{(1R,3S)-3-[5-Isopropyl-2-(3-methoxyphenyl)oxazol-4-ylmethoxy]cyclo-hexylmethoxy}-2-methylpropionic acid is obtained in analogy to Example 1 from tert-butyl 2-((1R,3S)-3-hydroxycyclohexylmethoxy)-2-methylpropionate and 4-iodomethyl-2-(3-methoxyphenyl)-5-isopropyloxazole.

C25H35NO6 (445.25): LCMS (ESI): 446.27 [MH+].

Example 10 tert-Butyl 2-methyl-2-[(1R,3S)-3-(tetrahydropyran-2-yloxy)cyclohexylmethoxy]pent-4-enoate

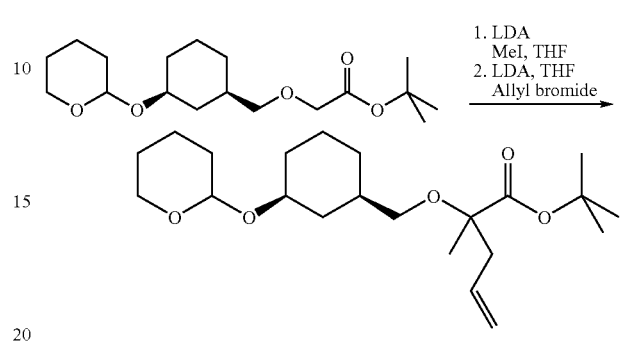

15 tert-Butyl 2-methyl-2-[(1R,3S)-3-(tetrahydropyran-2-yloxy)cyclohexylmethoxy]pent-4-enoate is obtained as a mixture of two diastereomers from tert-butyl [(1R,3S)-3-(tetrahydropyran-2-yloxy)cyclohexylmethoxy]acetate, methyl iodide, allyl bromide and lithium diisopropylamide in analogy to the synthesis of tert-butyl 2-methyl-2-[(1R ,3S)-3-(tetrahydropyran-2-yloxy)cyclohexylmethoxy]propionate in Example 1.

1H-NMR (500 MHz, DMSO): □=5.65-5.76 (m,1H), 5.04-5.13 (m, 2H), 4.68-4.72 (m, 1H); 3.73-3.80 (m, 1H); 3.44-3.53 (m, 1H); 3.38-3.44 (m, 1H); 3.06-3.2 (m, 2H); 2.55-2.63 (m, 1H); 2.32-2.45 (m, 2H);1.70-2.06 (m, 2H); 0.73-1.76 (m, 12H); 1.42 (s, 9H); 1.22 (s, 3H).

tert-Butyl 2-((1R ,3S)-3-hydroxycyclohexylmethoxy)-2-methylpent-4-enoate

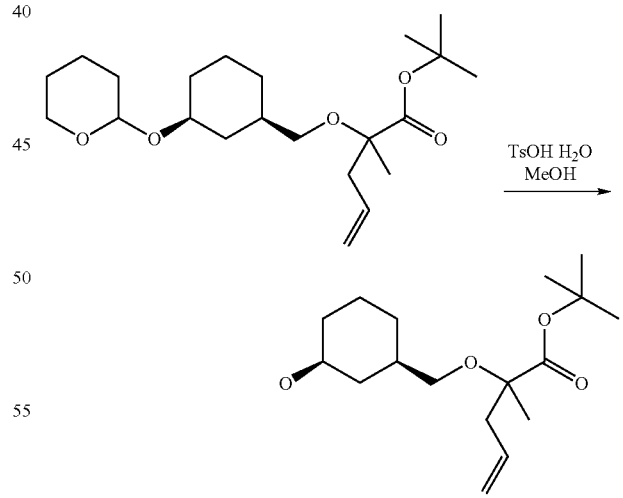

tert-Butyl 2-((1R,3S)-3-hydroxycyclohexylmethoxy)-2-methylpent-4-enoate is obtained as a mixture of two diastereomers from tert-butyl 2-methyl-2-[(1R,3S)-3-(tetrahydropyran-2-yloxy)cyclohexylmethoxy]pent-4-enoate and toluenesulfonic acid monohydrate in analogy to the synthesis of tert-butyl 2-((1R,3S)-3-hydroxycyclohexylmethoxy)-2-methylpropionate in Example 1.

1H-NMR (500 MHz, DMSO): ☐=5.65-5.76 (m, 1H), 5.04-5.13 (m, 2H), 4.45-4.48 (m, 1H); 3.29-3.36 (m,1H); 3.06-3.20 (m, 2H); 2.31-2.44 (m, 2H); 1.65-1.93 (m, 2H); 1.55-1.70 (m, 2H); 1.07-1.52 (m, 2H); 0.95-1.06 (m, 1H), 0.71-0.86 (m, 2H); 1.41 (s, 9H); 1.22 (s, 3H).

tert-Butyl 2-((1R,3S)-3-hydroxycyclohexylmethoxy)-2-methylpentanoate

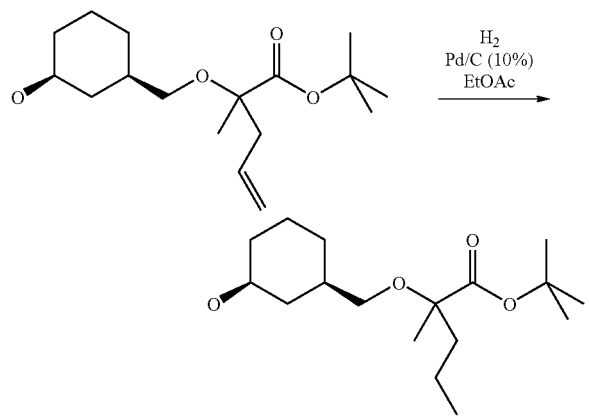

2.4 g of tert-butyl 2-((1R,3S)-3-hydroxycyclohexyl-methoxy)-2-methylpent-4-enoate are issolved in 15 ml of ethyl acetate and, under an argon atmosphere in an autoclave, a patula tip of Pd/C (10%) is added. The autoclave is then flushed with H₂, and the solution is stirred with an H₂ pressure of 3 bar at RT overnight. The catalyst is then iltered off through Celite, and the filtrate is concentrated, resulting in 2.3 g of tert-butyl 2-((1R,3S)-3-hydroxycyclohexylmethoxy)-2-methylpentanoate as a mixture of two iastereomers as pale yellow oil.

C17H32O4 (300.44); MS (Cl+): 301.5 (24) [MH⁺], 245.4 (100) [MH⁺-C4H8], 227 (18), 113 (58).

tert-Butyl 2-{(1R,3S)-3-[5-ethyl-2-(3-methoxyphenyl)oxazol-4-ylmethoxy]-cyclohexylmethoxy}-2-methylpentanoate

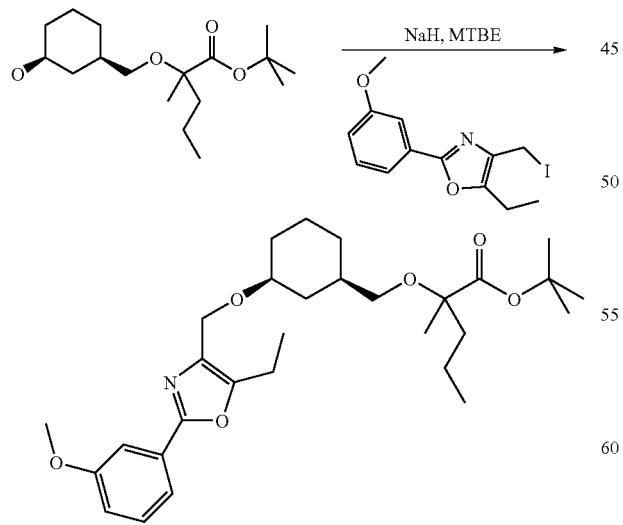

tert-Butyl 2-{(1R ,3S)-3-[5-ethyl-2-(3-methoxyphenyl) oxazol-4-ylmethoxy]-cyclohexylmethoxy}-2-methylpentanoate is obtained as a mixture of two diastereomers from tert-butyl 2-((1R,3S)-3-hydroxycyclohexylmethoxy)-2-methylpentanoate and tert-butyl 4-iodomethyl-5-ethyl-2-(3-methoxyphenyl)oxazole in analogy to the synthesis of tert-butyl 2-{(1R,3S)-3-[5-ethyl-2-(3-methoxyphenyl)oxazol-4-ylmethoxy]-cyclohexylmethoxy}-2-methylpropionate in Example 1.

C30H45NO6 (515.32): LCMS (ESI): 516.41 [MH⁺].

2-{(1R,3S )-3-[5-Ethyl-2-(3-methoxyphenyl)oxazol-4-ylmethoxy]cyclohexylmethoxy}-2-methylpentanoic acid

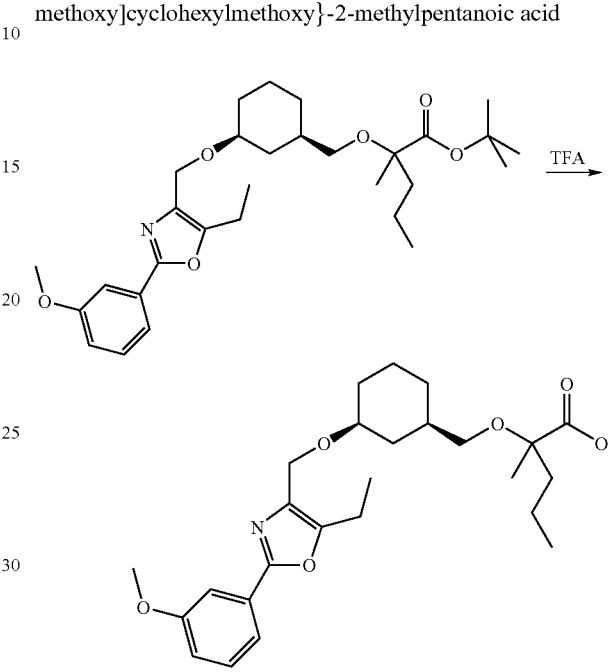

2-{(1R,3S)-3-[5-Ethyl-2-(3-methoxyphenyl)oxazol-4-ylmethoxy]cyclohexylmethoxy}-2-methylpentanoic acid is obtained as a mixture of two diastereomers from tert-butyl 2-((1R,3S)-3-hydroxycyclohexylmethoxy)-2-methylpentanoate and trifluoroacetic acid in analogy to the synthesis of 2-{(1R,3S)-3-[5-ethyl-2-(3-methoxyphenyl)oxazol-4-ylmethoxy]cyclohexylmethoxy}-2-methylpropionic acid in Example 1.

C26H37NO6 (459.26): LCMS (ESI): 459.58 [MH⁺].

Example 11

2-[(1R,3S)-3-(5-Ethyl-2-p-tolyloxazol-4-ylmethoxy)cyclohexylmethoxy]-2-methyl-pentanoic acid

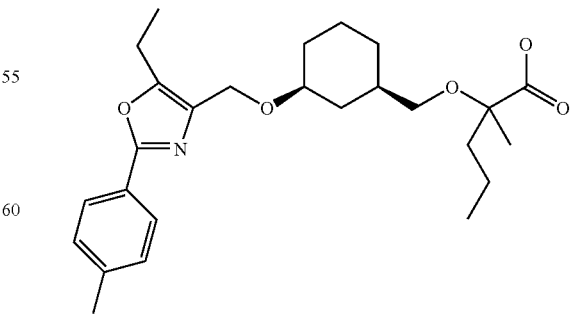

2-[(1R ,3S)-3-(5-Ethyl-2-p-tolyloxazol-4-ylmethoxy)cyclohexylmethoxy]-2-methylpentanoic acid is obtained as a mixture of two diastereomers from tert-butyl 2-((1R,3S)-3-hydroxycyclohexylmethoxy)-2-methylpentanoate and 4-iodomethyl-5-ethyl-2-p-tolyloxazole in analogy to Example 10.

C26H37NO5 (443.27): LCMS (ESI): 488.53 [M+HCOO].

Example 12

2-{(1R,3S)-3-[5-Ethyl-2-(4-isobutylphenyl)oxazol-4-ylmethoxy]cyclohexylmethoxy}-2-methylpentanoic acid

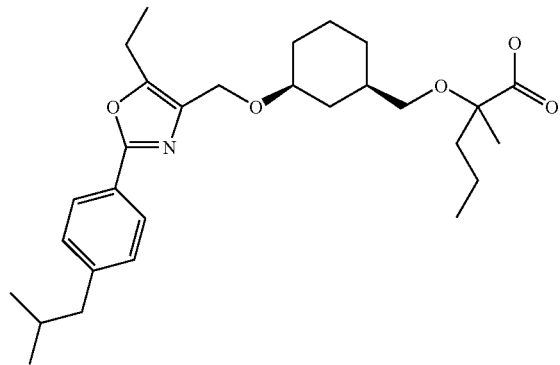

2-{(1R,3S)-3-[5-Ethyl-2-(4-isobutylphenyl)oxazol-4-ylmethoxy]cyclohexylmethoxy}-2-methylpentanoic acid is obtained as a mixture of two diastereomers from tert-butyl 2-((1R,3S)-3-hydroxycyclohexylmethoxy)-2-methylpentanoate and 4-iodomethyl-5-ethyl-2-(4-isobutylphenyl)oxazole in analogy to Example 10.

C29H43NO5 (485.31): LCMS (ESI): 485.49 [MH+].

Example 13

2-{(1R,3S)-3-[5-Ethyl-2-(naphth-2-yl)oxazol-4-ylmethoxy]cyclohexylmethoxy}-2-methylpentanoic acid

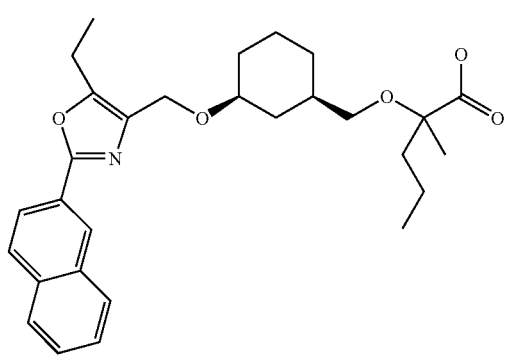

2-{(1R,3S)-3-[5-Ethyl-2-(naphth-2-yl)oxazol-4-ylmethoxy]cyclohexylmethoxy}-2-methylpentanoic acid is obtained as a mixture of two diastereomers from tert-butyl 2-((1R,3S)-3-hydroxycyclohexylmethoxy)-2-methylpentanoate and 5-ethyl-4-iodomethyl-2-(naphth-2-yl))oxazole in analogy to Example 10.

C29H37NO5 (479.27): LCMS (ESI): 524.52 [M+HCOO].

Example 14

2-{(1R,3S)-3-[5-Ethyl-2-(4-isopropylphenyl)oxazol-4-ylmethoxy}cyclohexylmethoxy]-2-methylpentanoic acid

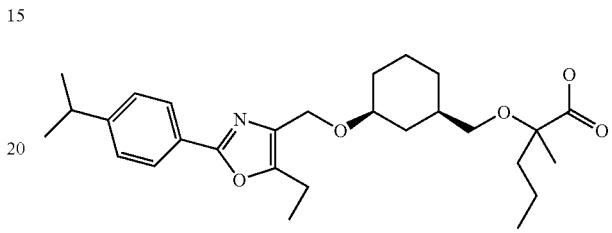

2-{(1R,3S)-3-[5-Ethyl-2-(4-isopropylphenyl)oxazol-4-ylmethoxy]cyclohexylmethoxy}-2-methylpentanoic acid is obtained as a mixture of two diastereomers from tert-butyl 2-((1R,3S)-3-hydroxycyclohexylmethoxy)-2-methylpentanoate and 5-ethyl-4-iodomethyl-2-(4-isopropylphenyl)oxazole in analogy to Example 10.

C29H37NO5 (479.27): LCMS (ESI): 524.52 [M+HCOO].

Example 15

2-Methyl-2-{(1R,3S)-3-[5-methyl-2-(naphth-2-yl)oxazol-4-ylmethoxy]-cyclohexylmethoxy}pentanoic acid

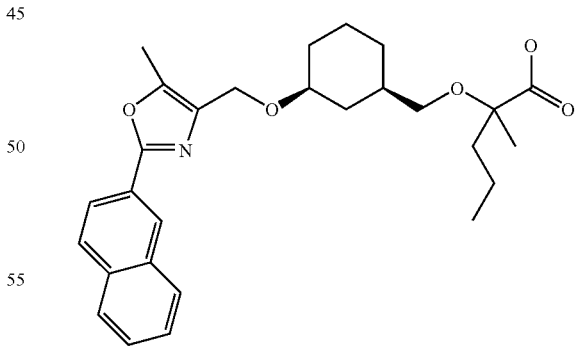

2-Methyl-2-{(1R,3S)-3-[5-methyl-2-(naphth-2-yl)oxazol-4-ylmethoxy]-cyclohexylmethoxy}pentanoic acid is obtained as a mixture of two diastereomers from tert-butyl 2-((1R,3S)-3-hydroxycyclohexylmethoxy)-2-methylpentanoate and 5-methyl-4-iodomethyl-2-(naphth-2-yl)oxazole in analogy to Example 10.

C28H35NO5 (465.25): LCMS (ESI): 510.57 [M+HCOO].

Example 16 tert-Butyl 2-methyl-3-phenyl-2-[(1R,3S)-3-(tetrahydropyran-2-yloxy)cyclohexyl-methoxy]propionate

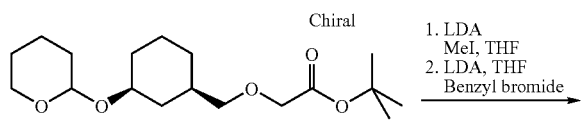

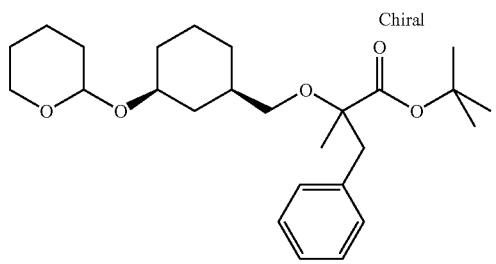

tert-Butyl 2-methyl-3-phenyl-2-[(1R,3S)-3-(tetrahydropyran-2-yloxy)-cyclohexylmethoxy]propionate is obtained as a mixture of two diastereomers from tert-butyl [(1R,3S)-3-(tetrahydropyran-2-yloxy)cyclohexylmethoxy]acetate, methyl iodide, benzyl bromide and lithium diisopropylamide in analogy to the synthesis of tert-butyl 2-methyl-2-[(1R,3S)-3-(tetrahydropyran-2-yloxy)cyclohexylmethoxy]propionate in Example 1.

C26H40O5 (432.29): LCMS (ESI): 450.34 (13) [M$^+$+H2O]; 349.25 (22) [M-C5H8O]; 293.17 (100) [M-C5H8O—C4H8].

tert-Butyl 2-((1R ,3S)-3-hydroxycyclohexylmethoxy)-2-methyl-3-phenylpropionate

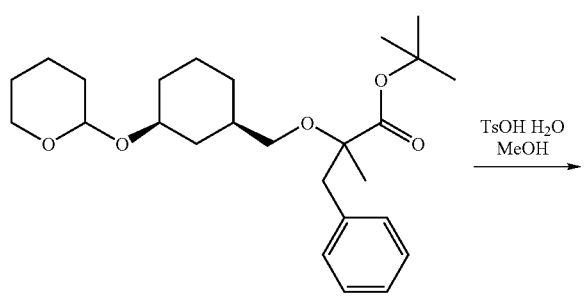

tert-Butyl 2-((1R,3S)-3-hydroxycyclohexylmethoxy)-2-methyl-3-phenylpropionate is obtained as a mixture of two diastereomers from tert-butyl 2-methyl-3-phenyl-2-[(1R, 3S)-3-(tetrahydropyran-2-yloxy)cyclohexylmethoxy]propionate and toluenesulfonic acid monohydrate in analogy to the synthesis of tert-butyl 2-((1R,3S)-3-hydroxycyclohexylmethoxy)-2-methylpropionate in Example 1.

C21H32O4 (348.23); MS (Cl+): 349.6 (38) [MH$^+$], 293.4 (100) [MH$^+$-C4H8], 247.4 (18), 113.4(19).

tert-Butyl 2-{(1R ,3S)-3-[5-ethyl-2-(3-methoxyphenyl)oxazol-4-ylmethoxy]-cyclohexylmethoxy}-2-methyl-3-phenylpropionate

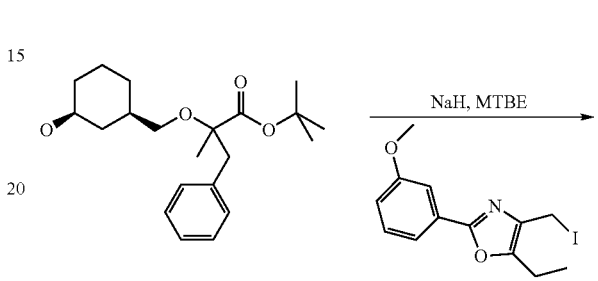

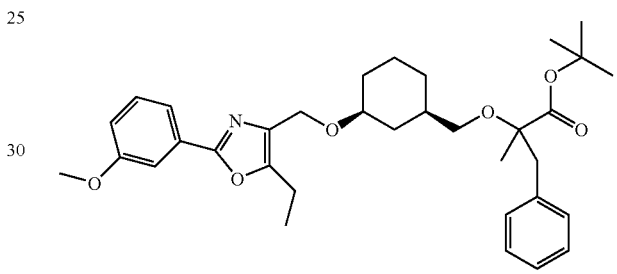

tert-Butyl 2-{(1R,3S)-3-[5-ethyl-2-(3-methoxyphenyl)oxazol-4-ylmethoxy]-cyclohexylmethoxy}-2-methyl-3-phenylpropionate is obtained as a mixture of two diastereomers from tert-butyl 2-((1R,3S)-3-hydroxycyclohexylmethoxy)-2-methyl-3-phenylpropionate and 4-iodmethyl-5-ethyl-2-(3-methoxyphenyl)oxazole in analogy to the synthesis of tert-butyl 2-{(1R,3S)-3-[5-ethyl-2-(3-methoxyphenyl)oxazol-4-ylmethoxy]cyclohexylmethoxy}-2-methylpropionate in Example 1.

C34H45NO6 (563.32): LCMS (ESI): 564.46 [MH$^+$].

2-{(1R,3S)-3-[5-Ethyl-2-(3-methoxyphenyl)oxazol-4-ylmethoxy]cyclohexylmethoxy}-2-methyl-3-phenylpropionic acid

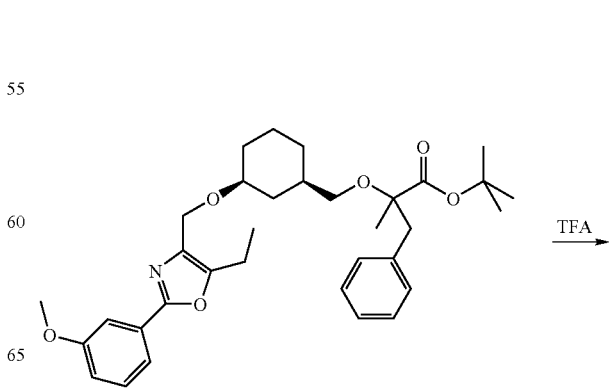

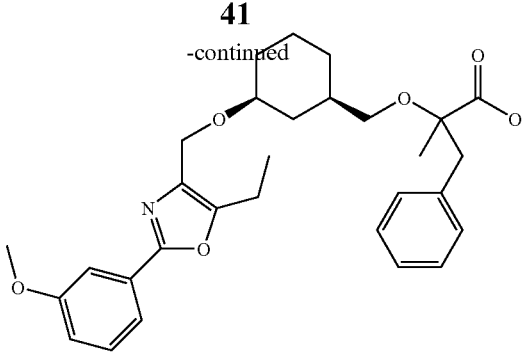

2-{(1R,3S)-3-[5-Ethyl-2-(3-methoxyphenyl)oxazol-4-yl-methoxy]cyclohexylmethoxy}-2-methyl-3-phenylpropionic acid is obtained as a mixture of two diastereomers from tert-butyl 2-{(1R,3S)-3-[5-ethyl-2-(3-methoxyphenyl)oxazol-4-ylmethoxy]-cyclohexylmethoxy}-2-methyl-3-phenylpropionate and trifluoroacetic acid in analogy to the synthesis of 2-{(1R,3S)-3-[5-ethyl-2-(3-methoxyphenyl)oxazol-4-ylmethoxy]-cyclohexylmethoxy}-2-methylpropionic acid in Example 1.

C30H37NO6 (507.26): LCMS (ESI): 508.40 [MH+].

Example 17

2-[(1R,3S)-3-(5-Ethyl-2-p-tolyloxazol-4-ylmethoxy)cyclohexylmethoxy]-2-methyl-3-phenylpropionic acid

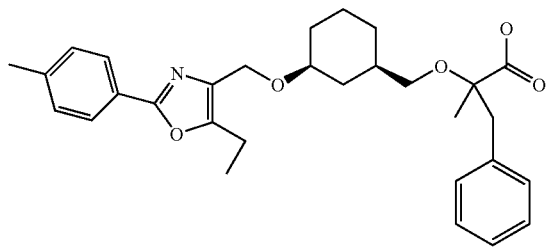

2-[(1R,3S)-3-(5-Ethyl-2-p-tolyloxazol-4-ylmethoxy)cyclohexylmethoxy]-2-methyl-3-phenylpropionic acid is obtained as a mixture of two diastereomers from tert-butyl 2-((1R,3S)-3-hydroxycyclohexylmethoxy)-2-methyl-3-phenylpropionate and 4-iodomethyl-5-ethyl-2-p-tolyloxazole in analogy to Example 10.

C30H37NO5 (491.27: LCMS (ESI): 492.40 [MH+].

Example 18

2-{(1R,3S)-3-[5-Ethyl-2-(4-isobutylphenyl)oxazol-4-ylmethoxy]cyclohexylmethoxy}-2-methyl-3-phenylpropionic acid

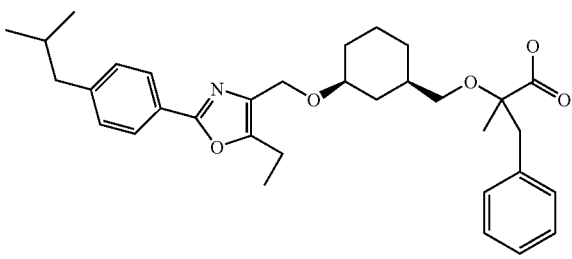

2-{(1R,3S)-3-[5-Ethyl-2-(4-isobutylphenyl)oxazol-4-yl-methoxy]cyclohexylmethoxy}-2-methyl-3-phenylpropionic acid is obtained as a mixture of two diastereomers from tert-butyl 2-((1R,3S)-3-hydroxycyclohexylmethoxy)-2-methyl-3-phenylpropionate and 4-iodomethyl-5-ethyl-2-(4-isobutylphenyl)oxazole in analogy to Example 10.

C33H43NO5 (533.31): LCMS (ESI): 534.45 [MH+].

Example 19

2-{(1R,3S)-3-[5-Ethyl-2-(naphth-2-yl)oxazol-4-ylmethoxy]cyclohexylmethoxy}-2-methyl-3-phenylpropionic acid

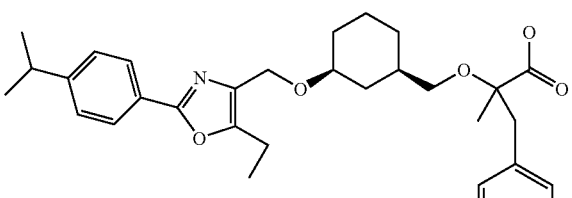

2-{(1R,3S)-3-[5-Ethyl-2-(naphth-2-yl)oxazol-4-ylmethoxy]cyclohexylmethoxy}-2-methyl-3-phenylpropionic acid is obtained as a mixture of two diastereomers from tert-butyl 2-((1R,3S)-3-hydroxycyclohexylmethoxy)-2-methyl-3-phenylpropionate and 5-ethyl-4-iodomethyl-2-(naphth-2-yl)oxazole in analogy to Example 10.

C33H37NO5 (527.27): LCMS (ESI): 528.40 [MH+].

Example 20

2-{(1R,3S)-3-[5-Ethyl-2-(4-isopropylphenyl)oxazol-4-ylmethoxy]cyclohexylmethoxy}-2-methyl-3-phenylpropionic acid 2-{(1R,3S)-3-[5-Ethyl-2-(4-isopropylphenyl)oxazol-4-ylmethoxy]cyclohexylmethoxy}-2-methyl-3-phenylpropionic acid is obtained as a mixture of two diastereomers from tert-butyl 2-((1R 3S)-3-hydroxycyclohexylmethoxy)-2-methyl-3-phenylpropionate and 5-ethyl-4-iodomethyl-2-(4-isopropylphenyl)oxazole in analogy to Example 10.

C32H41 NO5 (519.30): LCMS (ESI): 564.59 [M+HCOO].

Example 21

2-Methyl-2-{(1R,3S)-3-[5-methyl-2-(naphth-2-yl)oxazol-4-ylmethoxy]-cyclohexyimethoxy}-3-phenyl-propionic acid

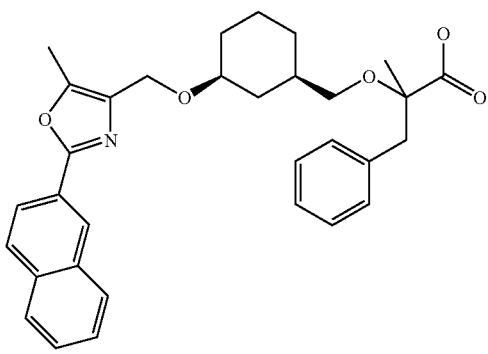

2-Methyl-2-{(1R,3S)-3-[5-methyl-2-(naphth-2-yl)oxazol-4-ylmethoxy]-cyclohexylmethoxy}-3-phenylpropionic acid is obtained as a mixture of two diastereomers from tert-butyl 2-((1R,3S)-3-hydroxycyclohexylmethoxy)-2-methyl-3-phenylpropionate and 5-methyl-4-iodomethyl-2-(naphth-2-yl)oxazole in analogy to Example 10.

C32H35NO5 (513.25): LCMS (ESI): 514.38 [MH$^+$].

What is claimed is:

1. A compound of formula I

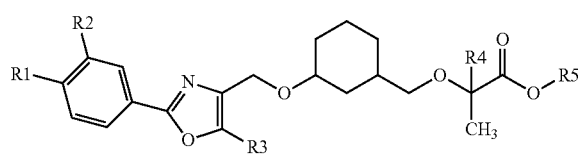

wherein:
R1 is H or (C1-C6)-alkyl;
R2 is selected from the group consisting of H, O-(C1-C3)-alkyl and CF$_3$; or
R1 and R2 may be fused together with the phenyl ring to form naphthyl;
R3 is ethyl or propyl;
R4 is selected from the group consisting of (C1-C6)-alkyl and benzyl; and
R5 is selected from the group consisting of H and (C1-C6)-alkyl;
or a suitable salt thereof.

2. The compound according to claim 1, wherein
R1 or R2 is H,
or a suitable salt thereof.

3. The compound according to claim 2 wherein
R4 is methyl,
or a suitable salt thereof.

4. A pharmaceutical composition comprising at least one compound according to claim 1, or a suitable salt thereof, and a pharmaceutically acceptable carrier.

5. The pharmaceutical composition according to claim 4 further comprises one or more additional secondary active ingredients selected from the group consisting of anti-diabetic agents, wherein the pharmaceutical composition is therapeutically effective when administered to a patient with diabetes or hyperglycemia.

6. A process for producing a pharmaceutical composition comprising at least one compound according to claim 1, or a suitable salt thereof, which comprises mixing one or more of the active ingredients of formula I with a pharmaceutically suitable carrier, and converting this mixture into a form suitable for administration.

7. A pharmaceutical composition comprising at least one compound according to claim 1, or a suitable salt thereof, and a pharmaceutically acceptable carrier.

8. A pharmaceutical composition comprising at least one compound according to claim 2, or a suitable salt thereof, and a pharmaceutically acceptable carrier.

9. A pharmaceutical composition comprising at least one compound according to claim 3, or a suitable salt thereof, and a pharmaceutically acceptable carrier.

10. A method for treating type-2 diabetes or dyslipidemia, in a patient in need thereof, comprising administering to the patient a pharmaceutically effective amount of the compound according to claim 1, or a suitable salt thereof.

11. A method for treating type-2 diabetes or dyslipidemia, in a patient in need thereof, comprising administering to the patient a pharmaceutically effective amount of the compound according to claim 2, or a suitable salt thereof.

12. A method for treating type-2 diabetes or dyslipidemia, in a patient in need thereof, comprising administering to the patient a pharmaceutically effective amount of the compound according to claim 3, or a suitable salt thereof.

13. A compound, which is
2-Methyl-2-{(1R,3S)-3-[5-methyl-2-(naphth-2-yl)oxazol-4-ylmethoxy]cyclo-hexylmethoxy}propionic acid;
2-Methyl-2-{(1R,3S)-3-[5-methyl-2-(naphth-2-yl)oxazol-4-ylmethoxy]-cyclohexylmethoxy}pentanoic acid; or
2-Methyl-2-{(1R,3S)-3-[5-methyl-2-(naphth-2-yl)oxazol-4-ylmethoxy]cyclohexylmethoxy}-3-phenylpropionic acid;
or a suitable salt thereof.

14. A pharmaceutical composition comprising at least one compound according to claim 13, or a suitable salt thereof, and a pharmaceutically acceptable carrier.

15. A method for treating type-2 diabetes or dyslipidemia, in a patient in need thereof, comprising administering to the patient a pharmaceutically effective amount of the compound according to claim 13, or a suitable salt thereof.

* * * * *